(12) United States Patent
Bond et al.

(10) Patent No.: US 11,106,347 B1
(45) Date of Patent: Aug. 31, 2021

(54) SYSTEMS AND METHODS FOR HIGH-SCALE TOP-DOWN DATA ANALYSIS

(71) Applicant: Palantir Technologies Inc., Palo Alto, CA (US)

(72) Inventors: Ethan Bond, New York, NY (US); Michael Nazario, New York, NY (US); Teofana Hadzhiganeva, Bethesda, MD (US); Devin Halladay, Strongsville, OH (US)

(73) Assignee: Palantir Technologies Inc., Denver, CO (US)

( * ) Notice: Subject to any disclaimer, the term of this patent is extended or adjusted under 35 U.S.C. 154(b) by 110 days.

(21) Appl. No.: 16/683,131

(22) Filed: Nov. 13, 2019

Related U.S. Application Data

(60) Provisional application No. 62/856,987, filed on Jun. 4, 2019.

(51) Int. Cl.
| | |
|---|---|
| *G06F 3/048* | (2013.01) |
| *G06F 3/0484* | (2013.01) |
| *G06F 3/0482* | (2013.01) |
| *G16H 50/70* | (2018.01) |
| *G16H 10/60* | (2018.01) |

(52) U.S. Cl.
CPC ........ *G06F 3/04847* (2013.01); *G06F 3/0482* (2013.01); *G16H 10/60* (2018.01); *G16H 50/70* (2018.01)

(58) Field of Classification Search
CPC .. G06F 3/04847; G06F 3/0482; G06F 16/322; G06F 40/014; G16H 50/70; G16H 10/60; H04N 1/00435; H04N 1/00429
See application file for complete search history.

(56) References Cited

U.S. PATENT DOCUMENTS

2012/0200507 A1* 8/2012 Flam ...................... G16H 15/00
                                                              345/173

* cited by examiner

*Primary Examiner* — Phuong H Nguyen
(74) *Attorney, Agent, or Firm* — Sheppard Mullin Richter & Hampton LLP

(57) ABSTRACT

Systems, methods, and non-transitory computer-readable media are provided for data analysis. A user interface comprising boards corresponding to one or more objects and one or more operations on the input and/or output objects of the boards can be generated for high-scale top-down data analysis.

20 Claims, 16 Drawing Sheets

SYSTEMS AND METHODS FOR HIGH-SCALE TOP-DOWN DATA ANALYSIS

CROSS REFERENCE TO RELATED APPLICATIONS

This application claims the benefit under 35 U.S.C. § 119(e) of U.S. Provisional Application No. 62/856,987, filed Jun. 4, 2019, the content of which is incorporated by reference in its entirety into the present disclosure.

TECHNICAL FIELD

This disclosure relates to user interface, more particularly, to user interface for high-scale data analysis.

BACKGROUND

Researchers and analysts may need to perform high-scale top-down data analysis. Existing technologies fail to provide such functionality with robust and intuitive graphical user interfaces and operations. For example, logical operations which are essential for particular types of research and analysis (e.g., medical research and analysis) are not provided in traditional solutions.

SUMMARY

A claimed solution rooted in computer technology overcomes problems specifically arising in the realm of computer technology. The claimed solution provides an improvement over existing technologies, for example, by providing a specific, structured graphical user interface that enables high-scale top-down data analysis.

Disclosed herein include embodiments of a system, method, and non-transitory computer readable medium for performing data analysis and/or generating a user interface for performing data analysis (e.g., for performing high-scale top-down data analysis and/or generating a user interface for performing high-scale top-down data analysis). In some embodiments, the system comprises: one or more processors; and memory storing instructions that, when executed by the one or more processors, cause the system to perform: generating a multi-level board user interface comprising a plurality of boards at different display levels. A first board of the plurality of boards can comprise an object board corresponding to a first object type of a plurality of object types. The plurality of boards can comprise a plurality of operation boards corresponding to a plurality of operations on the plurality of object types. Each of the plurality of boards, other than a last board, can be connected, via an inter-board path, to a next board of the plurality of boards. An output object type of each of the plurality of boards can be an input object type of the next board. An operation board can comprise (i) a first element connected, via an intra-board path, to (ii) a second element representing the input object type and the output object type of the operation board, respectively. The instructions, when executed by the one or more processors, can cause the system to perform: causing to display the multi-level board user interface.

In some embodiments, the plurality of object types comprises a subject object type, an action object type, and a detection object type. The subject object type can comprise a patient object type, wherein the action object type comprises a treatment object type, and the detection object type can comprise a diagnosis object type. The plurality of operation boards can comprise a filter operation board, a switch operation board, and an enrich operation board corresponding to the plurality of operations comprising a filter operation, a switch operation, and an enrich operation. The filter operation board can comprise one or more filter elements connected, via one or more intra-filter operation board paths, by one or more logic operations, the switch operation board can comprise (i) a first switch element connected, via an intra-switch operation board path, to (ii) a second switch element representing the input object type and the output object type of the switch operation, respectively, and/or the enrich operation board can comprise (i) a first enrich element representing the input object type of the enrich operation board connected, via a first intra-enrich operation board path and a second intra-enrich operation board path, respectively, to (ii) a second enrich element representing a second object type and (iii) a third enrich element representing the output object type, comprising a virtual object type representing a combination of the input object type of the enrich operation board and the third object type, of the enrich operation board.

Disclosed herein include embodiments of a system (e.g., for performing high-scale top-down data analysis and/or generating a user interface for performing high-scale top-down data analysis). In some embodiments, the system comprises: one or more processors; and memory storing instructions that, when executed by the one or more processors, cause the system to perform: generating a multi-level board user interface comprising a plurality of boards at different display levels, the plurality of boards comprising (i) an object board at a first display level and (ii) a plurality of operation boards each at a different second display level. In some embodiments, the object board corresponds to a first object type of a plurality of object types comprising a patient object type, a treatment object type, and a diagnosis object type. In some embodiments, the object board is connected, via a first inter-board path, to a first operation board of the plurality of operation boards. Each of the plurality of operation boards, other than a last operation board, can be connected, via a second inter-board path, to a next operation board of the plurality of operation boards. In some embodiments, an input object type of the first operation board comprises the first object type. An output object type of each of the plurality of operation boards can be an input object type of the next operation board. In some embodiments, the plurality of operation boards can correspond to a plurality of operations. The plurality of operations can comprise a filter operation, a switch operation, and an enrich operation. The plurality of operation boards can comprise a filter operation board, an enrich operation board, and a switch operation board. In some embodiments, the filter operation board can comprise one or more filter elements connected, via one or more intra-filter operation board paths, by one or more logic operations. The input type of the filter operation board and the output type of the filter operation board can be identical. In some embodiments, the switch operation board can comprise (i) a first switch element representing the input object type of the switch operation board and (ii) a second switch element representing the output object type of the switch operation board. The first switch element and the second switch element can be connected by a switch link element, via an intra-switch operation board path, representing a switch relationship between the input object type of the switch operation board and the output object type of the switch operation board. In some embodiments, the enrich operation board comprises (i) a first enrich element representing the input object type of the enrich operation board, (ii) a second enrich element representing a second object type of the plurality of object types, or a combination thereof, and (iii) a third enrich element representing the output object type of the enrich operation board, the output object type of the enrich operation board comprising a virtual object type representing a combination of the input object type of the enrich operation board and the second object type. In some embodiments, the first enrich element and the second enrich element are connected, via a first intra-enrich operation board path, by an enriching link element representing an enrich relationship between the input object type of the enrich operation board and the output object type of the enrich operation board. In some embodiments, the first enrich element is connected, via a second intra-enrich operation board path, to the third enrich element. The instructions, when executed by the one or more processors, can cause the system to display the multi-level board user interface.

In some embodiments, the object board comprises an object board body. Each of the plurality of operation boards can comprise an operation board header, an operation board body, and an operation board footer. The multi-level board user interface comprises the object board and operation boards of the plurality of operation boards that are arranged vertically, horizontally, or a combination thereof.

In some embodiments, the instructions, when executed by the one or more processors, cause the system to perform: receiving a user selection of the first object type. The instructions, when executed by the one or more processors, can cause the system to perform: receiving a user selection of each of the plurality of operations corresponding to the plurality of operation boards.

In some embodiments, the instructions, when executed by the one or more processors, cause the system to perform: generating an initial user interface comprising (i) the object board at the first display level connected to (ii) a plurality of selection elements at a second display level. The plurality of selection elements can correspond to the plurality of operations. The instructions, when executed by the one or more processors, cause the system to perform: provide the initial user interface for display to at least one device.

In some embodiments, the instructions, when executed by the one or more processors, cause the system to perform: receiving a user selection of the output object type of the switch operation board. The instructions, when executed by the one or more processors, can cause the system to perform: determining a plurality of switch relationships compatible with the input object type of the switch operation board and the output object type of the switch operation board. The instructions, when executed by the one or more processors, can cause the system to perform: receiving a user selection of the switch relationship of the plurality of switch relationships.

In some embodiments, the instructions, when executed by the one or more processors, cause the system to perform: receiving a user selection of the enrich relationship. The instructions, when executed by the one or more processors, can cause the system to perform: determining a plurality of second object types compatible with the input object type of the enrich operation board and the enrich relationship. The instructions, when executed by the one or more processors, can cause the system to perform: receiving a user selection of the second object type of the plurality of second object types.

In some embodiments, the instructions, when executed by the one or more processors, cause the system to perform: receiving an invalid user input with respect to a first element in an operation board of the plurality of operation boards. The instructions, when executed by the one or more processors, can cause the system to perform: generating an error user interface comprising an error message adjacent to, or overlapping, the first element in the operation board. The first element of the operation board may not be connected to a second element in the operation board, via a first intra-board path of the operation board and/or a next operation board of the operation board, via a second intra-board path of the operation board. The instructions, when executed by the one or more processors, can cause the system to perform: causing to display the third user interface.

In some embodiments, the instructions, when executed by the one or more processors, cause the system to perform: retrieving patient data for a plurality of patients, treatment data of the plurality of patients, and diagnosis information associated with the treatment data. Generating the multi-level board user interface can comprise generating the multi-level board user interface using the patient data, the treatment data, and the diagnosis information.

In some embodiments, the instructions, when executed by the one or more processors, cause the system to perform: adding the output object type of the enrich operation comprising the virtual object type to the plurality of object types. In some embodiments, the instructions, when executed by the one or more processors, cause the system to perform: generating a template comprising relationships between and within the object board and the plurality of operation boards. In some embodiments, the instructions, when executed by the one or more processors, cause the system to perform: generating an output file comprising (i) relationships between and within the object board and the plurality of operation boards and (ii) data associated with the patient object type, the retreatment object type, and the diagnosis object type. In some embodiments, the plurality of objects, the plurality of operations, the inter-board paths, and the intra-board paths represent an ontology. In some embodiments, a combination of the inter-board paths and the intra-board paths represent a path from the first object type to the output object type of a last board of the plurality of boards.

In some embodiments, the method comprises: generating a multi-level board user interface comprising a plurality of boards at different display levels. A first board of the plurality of boards can comprise an object board corresponding to a first object type of a plurality of object types. The plurality of boards can comprise a plurality of operation boards corresponding to a plurality of operations on the plurality of object types. Each of the plurality of boards, other than a last board, can be connected, via an inter-board path, to a next board of the plurality of boards. An output object type of each of the plurality of boards can be an input object type of the next board. An operation board can comprise (i) a first element connected, via an intra-board path, to (ii) a second element representing the input object type and the output object type of the operation board, respectively. The method can further comprise: causing to display the multi-level board user interface.

In some embodiments, method comprises: generating a multi-level board user interface comprising a plurality of boards at different display levels, the plurality of boards comprising (i) an object board at a first display level and (ii) a plurality of operation boards each at a different second display level. In some embodiments, the object board corresponds to a first object type of a plurality of object types comprising a patient object type, a treatment object type, and a diagnosis object type. In some embodiments, the object board is connected, via a first inter-board path, to a first operation board of the plurality of operation boards. Each of the plurality of operation boards, other than a last operation board, can be connected, via a second inter-board path, to a next operation board of the plurality of operation boards. In some embodiments, an input object type of the first operation board comprises the first object type. An output object type of each of the plurality of operation boards can be an input object type of the next operation board. In some embodiments, the plurality of operation boards can correspond to a plurality of operations. The plurality of operations can comprise a filter operation, a switch operation, and an enrich operation. The plurality of operation boards can comprise a filter operation board, an enrich operation board, and a switch operation board. In some embodiments, the filter operation board can comprise one or more filter elements connected, via one or more intra-filter operation board paths, by one or more logic operations. The input type of the filter operation board and the output type of the filter operation board can identical. In some embodiments, the switch operation board can comprise (i) a first switch element representing the input object type of the switch operation board and (ii) a second switch element representing the output object type of the switch operation board. The first switch element and the second switch element can be connected by a switch link element, via an intra-switch operation board path, representing a switch relationship between the input object type of the switch operation board and the output object type of the switch operation board. In some embodiments, the enrich operation board comprises (i) a first enrich element representing the input object type of the enrich operation board, (ii) a second enrich element representing a second object type of the plurality of object types, or a combination thereof, and (iii) a third enrich element representing the output object type of the enrich operation board, the output object type of the enrich operation board comprising a virtual object type representing a combination of the input object type of the enrich operation board and the second object type. In some embodiments, the first enrich element and the second enrich element are connected, via a first intra-enrich operation board path, by an enriching link element representing an enrich relationship between the input object type of the enrich operation board and the output object type of the enrich operation board. In some embodiments, the first enrich element is connected, via a second intra-enrich operation board path, to the third enrich element. The method can further comprise: causing to display the multi-level board user interface.

In some embodiments, the non-transitory computer readable medium comprising instructions that, when executed, cause one or more processors to perform: generating a multi-level board user interface comprising a plurality of boards at different display levels. A first board of the plurality of boards can comprise an object board corresponding to a first object type of a plurality of object types. The plurality of boards can comprise a plurality of operation boards corresponding to a plurality of operations on the plurality of object types. Each of the plurality of boards, other than a last board, can be connected, via an inter-board path, to a next board of the plurality of boards. An output object type of each of the plurality of boards can be an input object type of the next board. An operation board can comprise (i) a first element connected, via an intra-board path, to (ii) a second element representing the input object type and the output object type of the operation board, respectively. The instructions, when executed, can cause the one or more processors to perform: causing to display the multi-level board user interface.

In some embodiments, the non-transitory computer readable medium comprising instructions that, when executed, cause one or more processors to perform: generating a multi-level board user interface comprising a plurality of boards at different display levels, the plurality of boards comprising (i) an object board at a first display level and (ii) a plurality of operation boards each at a different second display level. In some embodiments, the object board corresponds to a first object type of a plurality of object types comprising a patient object type, a treatment object type, and a diagnosis object type. In some embodiments, the object board is connected, via a first inter-board path, to a first operation board of the plurality of operation boards. Each of the plurality of operation boards, other than a last operation board, can be connected, via a second inter-board path, to a next operation board of the plurality of operation boards. In some embodiments, an input object type of the first operation board comprises the first object type. An output object type of each of the plurality of operation boards can be an input object type of the next operation board. In some embodiments, the plurality of operation boards can correspond to a plurality of operations. The plurality of operations can comprise a filter operation, a switch operation, and an enrich operation. The plurality of operation boards can comprise a filter operation board, an enrich operation board, and a switch operation board. In some embodiments, the filter operation board can comprise one or more filter elements connected, via one or more intra-filter operation board paths, by one or more logic operations. The input type of the filter operation board and the output type of the filter operation board can identical. In some embodiments, the switch operation board can comprise (i) a first switch element representing the input object type of the switch operation board and (ii) a second switch element representing the output object type of the switch operation board. The first switch element and the second switch element can be connected by a switch link element, via an intra-switch operation board path, representing a switch relationship between the input object type of the switch operation board and the output object type of the switch operation board. In some embodiments, the enrich operation board comprises (i) a first enrich element representing the input object type of the enrich operation board, (ii) a second enrich element representing a second object type of the plurality of object types, or a combination thereof, and (iii) a third enrich element representing the output object type of the enrich operation board, the output object type of the enrich operation board comprising a virtual object type representing a combination of the input object type of the enrich operation board and the second object type. In some embodiments, the first enrich element and the second enrich element are connected, via a first intra-enrich operation board path, by an enriching link element representing an enrich relationship between the input object type of the enrich operation board and the output object type of the enrich operation board. In some embodiments, the first enrich element is connected, via a second intra-enrich operation board path, to the third enrich element. The instructions, when executed, can cause the one or more processors to perform: causing to display the multi-level board user interface.

These and other features of the systems, methods, and non-transitory computer readable media disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for purposes of illustration and description only and are not intended as a definition of the limits of the invention.

BRIEF DESCRIPTION OF THE DRAWINGS

Certain features of various embodiments of the present technology are set forth with particularity in the appended claims. A better understanding of the features and advantages of the technology will be obtained by reference to the following detailed description that sets forth illustrative embodiments, in which the principles of the invention are utilized, and the accompanying drawings of which:

Figure 1A:
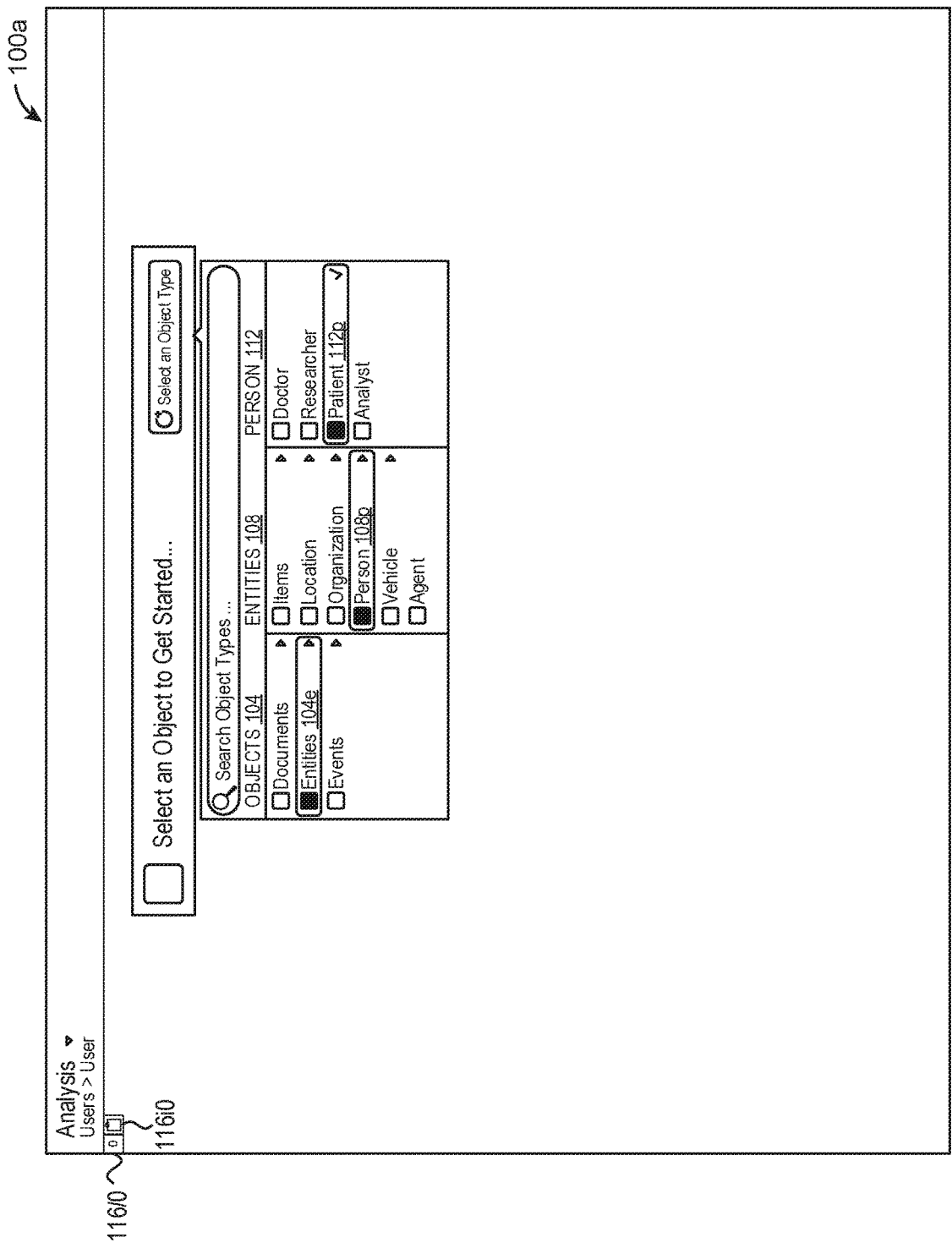
FIGS. 1A-1D illustrate example user interfaces for performing data analysis (e.g., high-scale top-down data analysis).

The figures depict various embodiments of the disclosed technology for purposes of illustration only, wherein the figures use like reference numerals to identify like elements. One skilled in the art will readily recognize from the following discussion that alternative embodiments of the structures and methods illustrated in the figures can be employed without departing from the principles of the disclosed technology described herein.

DETAILED DESCRIPTION

A claimed solution rooted in computer technology overcomes problems specifically arising in the realm of computer technology. The claimed solution provides an improvement over existing technologies, for example, by providing a specific, structured graphical user interface that enables high-scale top-down data analysis.

In various implementations, a computing system is configured to generate a multi-level board user interface, and causes the multi-level board user interface to be displayed to a user. For example, elements and/or paths of the multi-level board user interface may be represented in a manner that is similar to a circuit diagram, rather than a traditional data pipeline. The multi-level board user interface can comprise a plurality of boards at different display levels. For example, the multi-level board user interface can comprise (i) an object board at a first display level and (ii) a plurality of operation boards each at a different second display level. The object board can correspond to an object type (e.g., a patient object type, a treatment object type, a diagnosis object type). Object types may be defined by an ontology.

In some embodiments, an operation board can correspond to operations, such as a filter operation, a switch operation, and an enrich operation. An operation board can be a filter operation board, an enrich operation board, or a switch operation board.

In some embodiments, the object board is connected to the first operation board (e.g., via a first inter-board path). Each operation board, other than the last operation board, can be connected to the next operation board (e.g., via a second inter-board path). The input object type of each operation board is the output object type of the preceding operation board (or the object board for the first operation board).

In some embodiments, the filter operation board comprises one or more filter elements (e.g., elements representing filters such as patients younger than 40) connected (e.g., via one or more intra-filter operation board paths) by one or more logic operations (e.g., and, or, xor, not). The input type and the output type of the filter operation board can be identical.

In some embodiments, the switch operation board comprises (i) a first switch element representing the input object type (e.g., the patient object type) of the switch operation board and (ii) the output object type of the switch operation board (e.g., the treatment object type). The first switch element and the second switch element can be connected (e.g., via an intra-switch operation board path) by a switch link element representing a switch relationship (e.g., particular treatments the patients received) between the input object type of the switch operation board and the second object type.

In some embodiments, the enrich operation board comprises (i) a first enrich element representing the input object type (e.g., the treatment object type) of the enrich operation board, (ii) a second enrich element representing a third object type (e.g. the diagnosis object type) (iii) and a third enrich element representing the output object type of the enrich operation board and comprising a virtual object type (e.g., a virtual object including treatments with diagnoses). The virtual object type may be a temporary object representing a combination (e.g., a logical combination) of different object types, such as the input object type of the enrich operation board and the third object type. Virtual object types may not be represented in the ontology, but may nonetheless inherit functionality of the ontology. Virtual object types may become permanent object types and added to the ontology (e.g., in response to user input). The first enrich element and the second enrich element can be connected (e.g., via a first intra-enrich operation board path) by an enriching link element representing an enrich relationship between the input object type of the enrich operation board and the output object type of the enrich operation board. The first enrich element can be connected to the third enrich element (e.g., via a second intra-enrich operation board path).

Data Analysis

FIGS. 1A-1D illustrate example user interfaces for performing data analysis (e.g., high-scale top-down data analysis). A user (e.g., a researcher such as a cancer researcher) can start the data analysis process using an object type selector. A user can use a user interface to browse and select an object type category, drill down into a specific entity type, and then select a specific ontological or object type to start the data analysis process for a display level. FIG. 1A shows an example user interface 100a that prompts a user to browse and select an object type category 104 of possible object categories, then browse and select a specific entity type 108 of possible entity types, and then browse and select a specific ontological or object type 112 of possible ontological or object types to start the data analysis process for a first display level (the display level "0" 11610 shown). FIG. 1A shows that the user has selected the "Entities" object category 104e, the "Person" entity type 108p, and the "Patient" ontological or object type 112p. A zero state can refer to a state before the user begins browsing and selecting an object type category, a specific entity type, and a specific ontological or object type or before a specific ontological or object type is selected. Additional information such as notes related to the object type at this display level (e.g., how the objects of the object types are selected) can be added or modified using the notes icon 116i0.

Figure 1B:
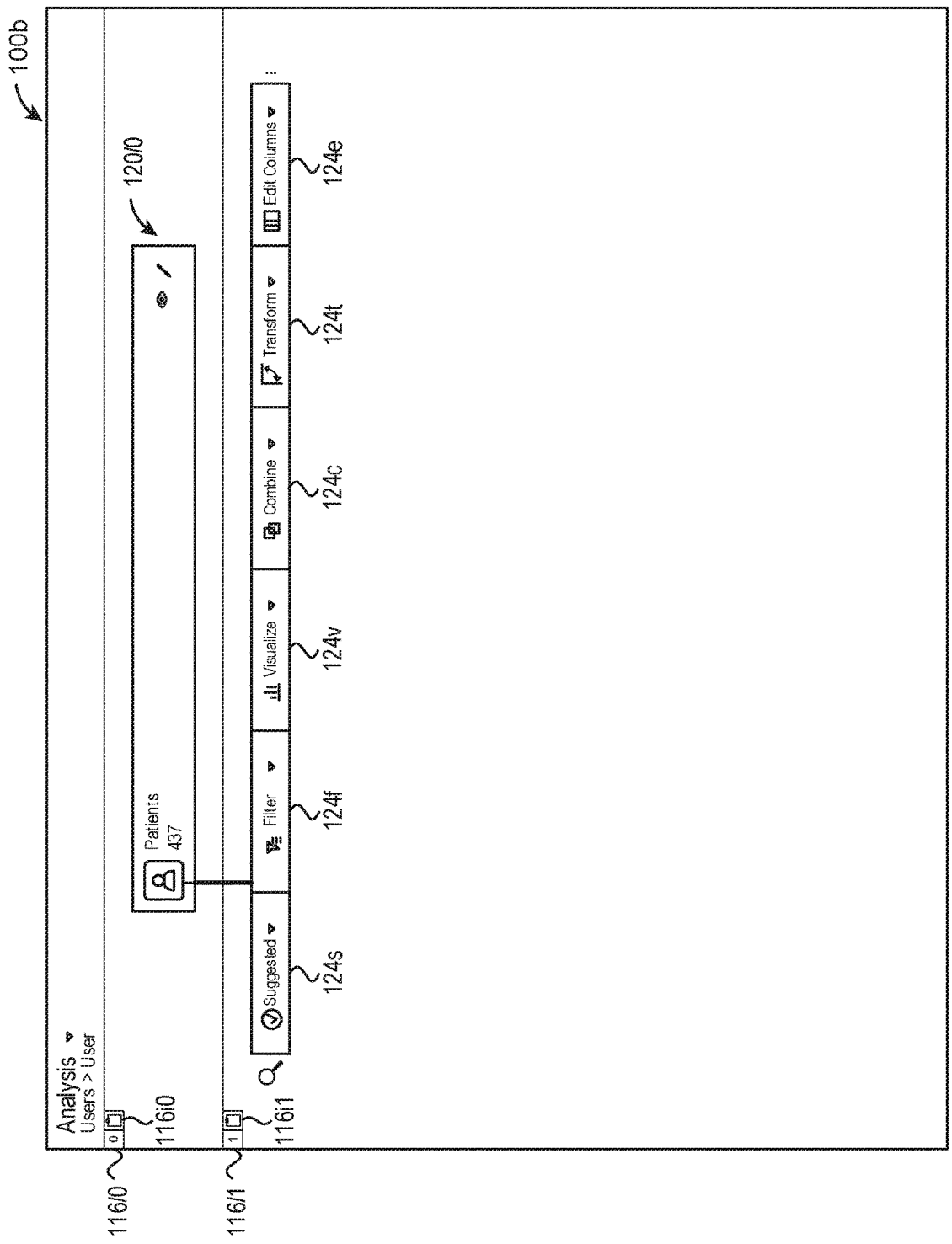

After selecting the object type using the user interface 100a illustrated in FIG. 1A, an updated user interface that includes an object board corresponding to or representing the selected ontological or object type at the first display level can be generated and presented to the user. FIG. 1B shows an example updated user interface 100b with an object board 120/0, corresponding to or representing the selected "Patient" ontological or object type 112p, at the first display level, that can be generated and presented to the user. The updated user interface can prompt the user to select an operation for the ontological or object type that user has selected at a second display level. FIG. 1B shows that the updated user interface 100b can include visual representations 124s, 124f, 124v, 124c, 124t, 124e (e.g., buttons) corresponding to or representing possible operations for the selected ontological or object type at the second display level (the display level "1" 116/1 shown). For example, the user can select the "Filter" operation for the "Patient" ontological or object type. Additional information such as notes related to the operation at this display level (e.g., rationales for the operation) can be added or modified using the notes icon 116i1.

Figure 1C:
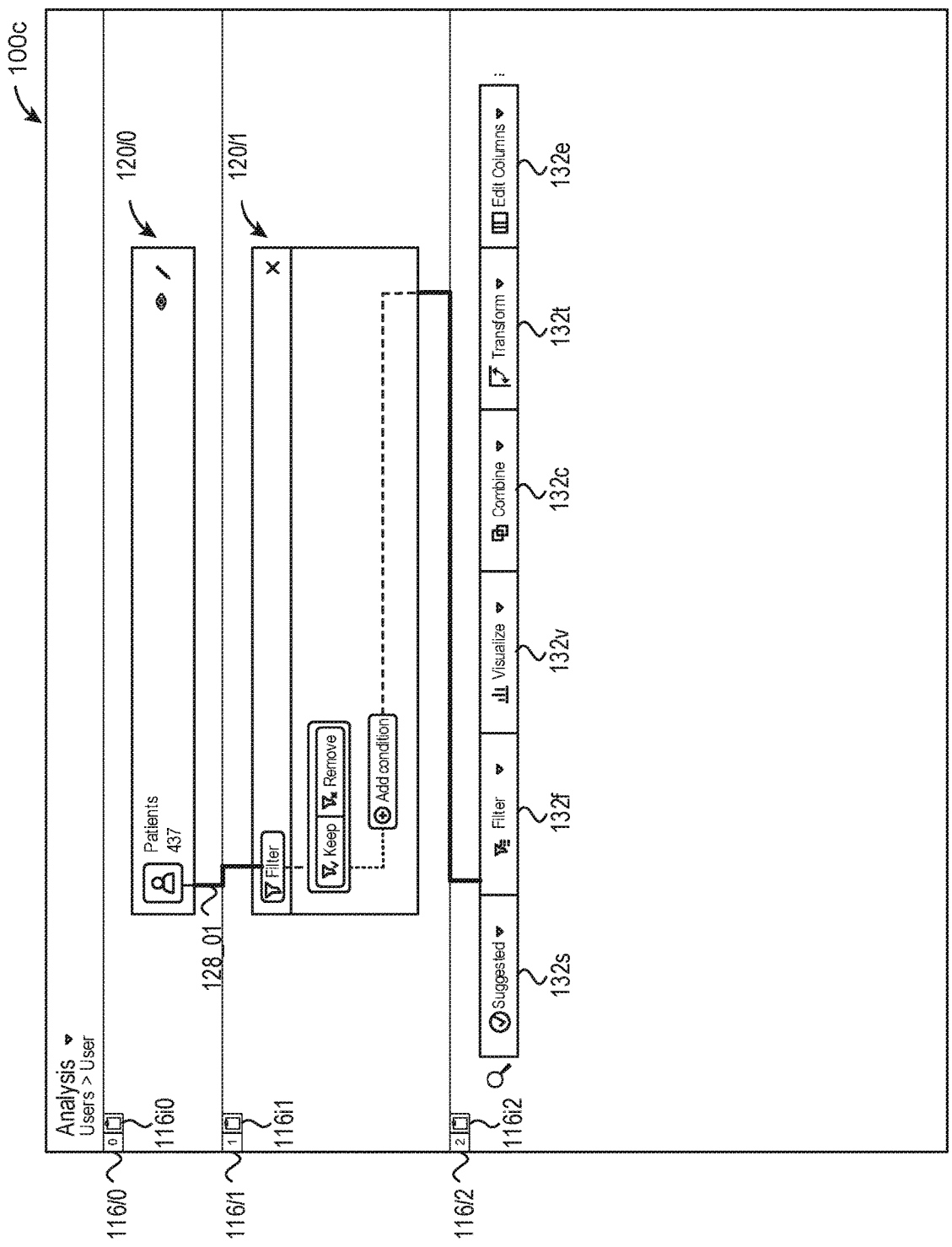

After selecting the operation for the selected ontological or object type at the second display level using the user interface 100b illustrated in FIG. 1B, a further updated user interface that includes an operation board corresponding to or representing the selected operation at the second display can be generated and presented to the user. FIG. 1C shows an example further updated user interface 100c with an operation board 120/1 corresponding to or representing the selected "Filter" operation at the second level (the display level "2" 116/2 shown). FIG. 1C shows that the selected "Patients" ontological or object type is the input of the "Filter" operation and the updated user interface 100c can include the corresponding object board 120/0 and operation board 120/1 linked via a path 128_01. An example filter operation board 500 is described herein with reference to FIG. 5. The updated user interface 100c can include visual representations 132s, 132f, 132v, 132c, 132t, 132e (e.g., buttons) corresponding to or representing possible operations for the output of the selected operation at the third display level (the display level "2" 116/2 shown). Additional information such as notes related to the operation at this display level can be added or modified using the notes icon 116i2.

Figure 1D:
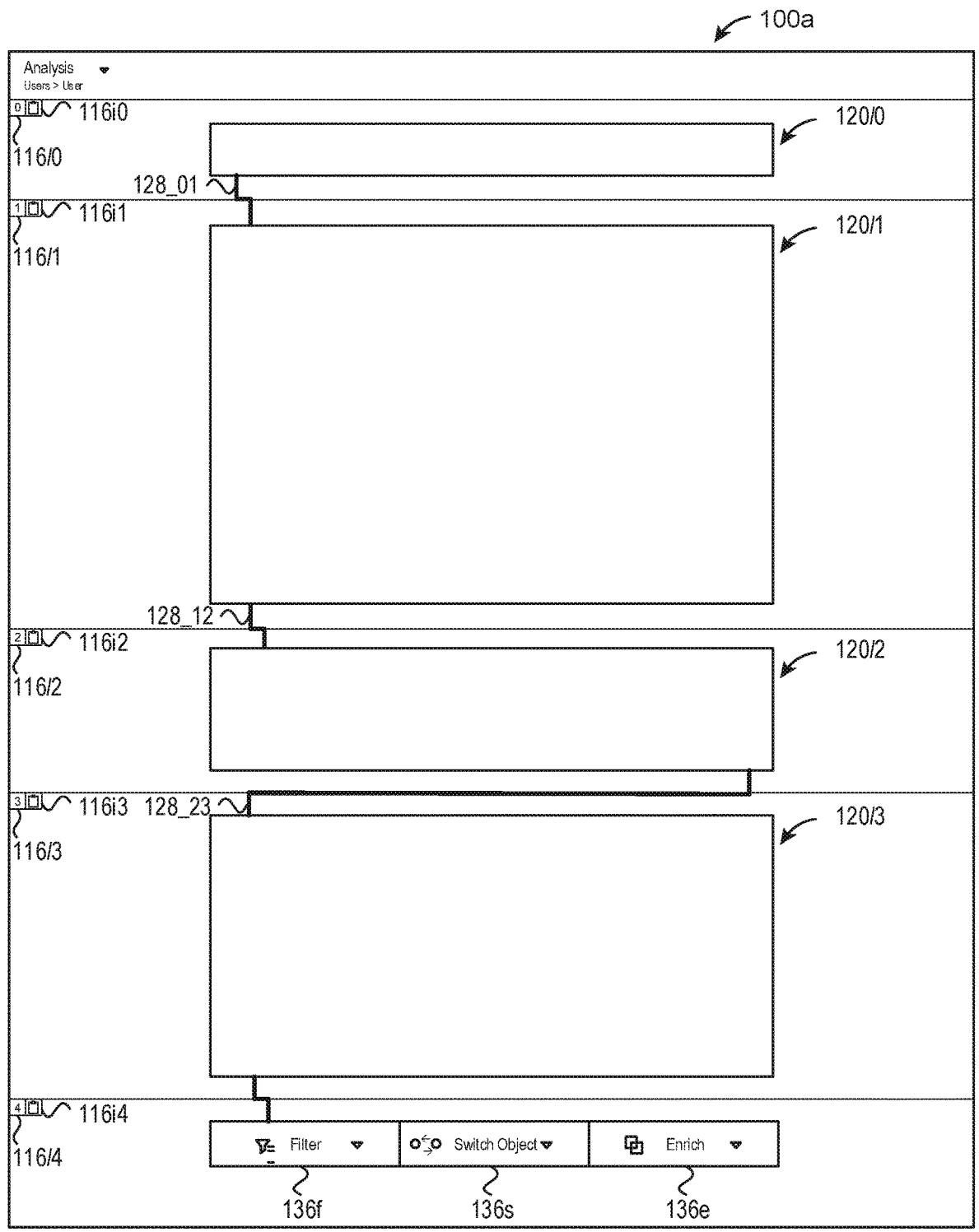

After selecting additional operations using the user interface 100c illustrated in FIG. 1C, another updated user interface that includes the object board 120/0 at the first level and the operation boards corresponding to or representing the selected operations at second, third, and fourth levels can be generated and presented to the user. FIG. 1D shows another example further updated user interface 100d that includes the object board 12010 at the first level and the operation boards 120/1-120/3 at the second, third, and fourth level (the display level "3" 11613 shown) can be generated. FIG. 1D shows that the output of the an operation board can be the input of a subsequent (e.g., immediate subsequent) operation board and the updated user interface 100d can include the successive operation boards 12011, 12012, 12013 linked via paths 128_12, 128_23 (shown as thicker solid lines in the figure). Example operation boards include a filter operation board 500, a switch operation board 600, an enrich operation board 700 are described herein with reference to FIGS. 5, 6, and 7, respectively. The updated user interface 100d can include visual representations 136f, 136s, 136e (e.g., buttons), corresponding to or representing possible operations for the output of the selected operation at the fourth level, at the fifth level (the display level "4" 11614 shown). Additional information such as notes related to the object type of each display level (including the input object type and the output object type) or the operation at each display level can be added or modified using the notes icons 116i0-116i4. The operations represented by the boards and the object type(s) of the input and output of the operations can be part of or form an ontology. Objects of the boards (e.g., objects of the input object type and output object types of an operation board) can be retrieved from one or more databases.

The path from the object board 12010 at the first display level/display level "0" to the operation board 12011 at the second display level/display level "1" via the path 128_01, to the operation board 12012 at the third display level/display level "2" via the path 128_12, to the operation board 12013 at the fourth display level/display level "3" via the path 128_23 can represent hypotheses and operations on the outputs of the preceding hypotheses and operations. The path can be zero-indexed, beginning at position 0. A hypothesis that branches off of another hypothesis can inherit the position of that hypothesis.

Board, Types, Anatomies, and Connections

There can be two or more classifications or types of boards, such as an object board type and a logic or operation board type. There can be three or more types of operation boards, such as a filter operation board type, an enrich operation board type, and a switch or pivot operation board type.

Figure 2:
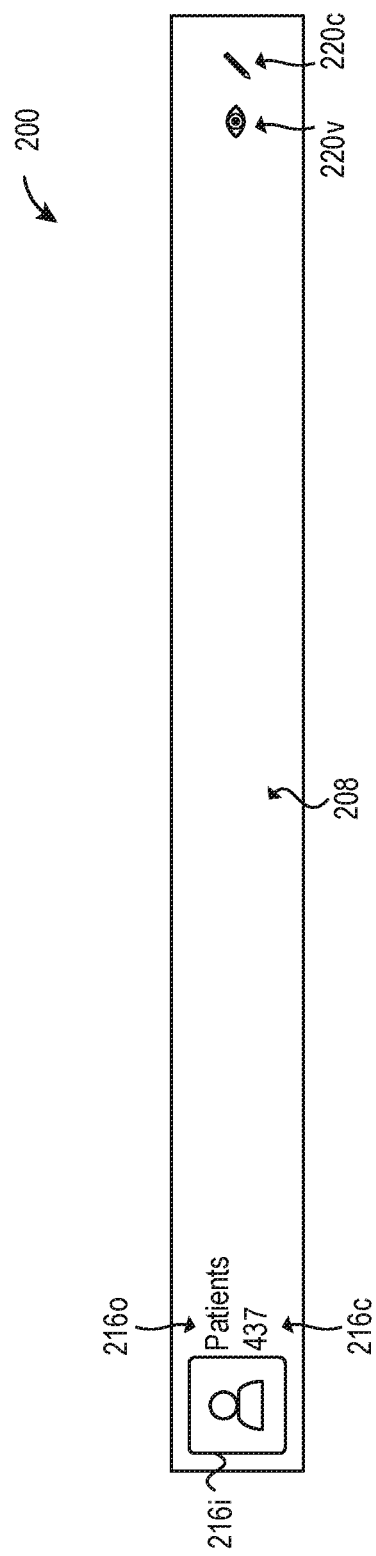
FIG. 2 illustrates an example patient object board.

An object board can include a board body. A board header can visually explain, describe, and/or summarize the object represented by the board. FIG. 2 shows an example object board 200 with a board body 208. The example object board 200 illustrated in FIG. 2 includes an object type icon 216i, an object type 216o (e.g., a string), and an object type count 216c (e.g., a string) on the left side of the board body 208. The board body 208 can include one or more action icons, such as the view object action icon 220v and the change type action icon 220c.

Figure 3:
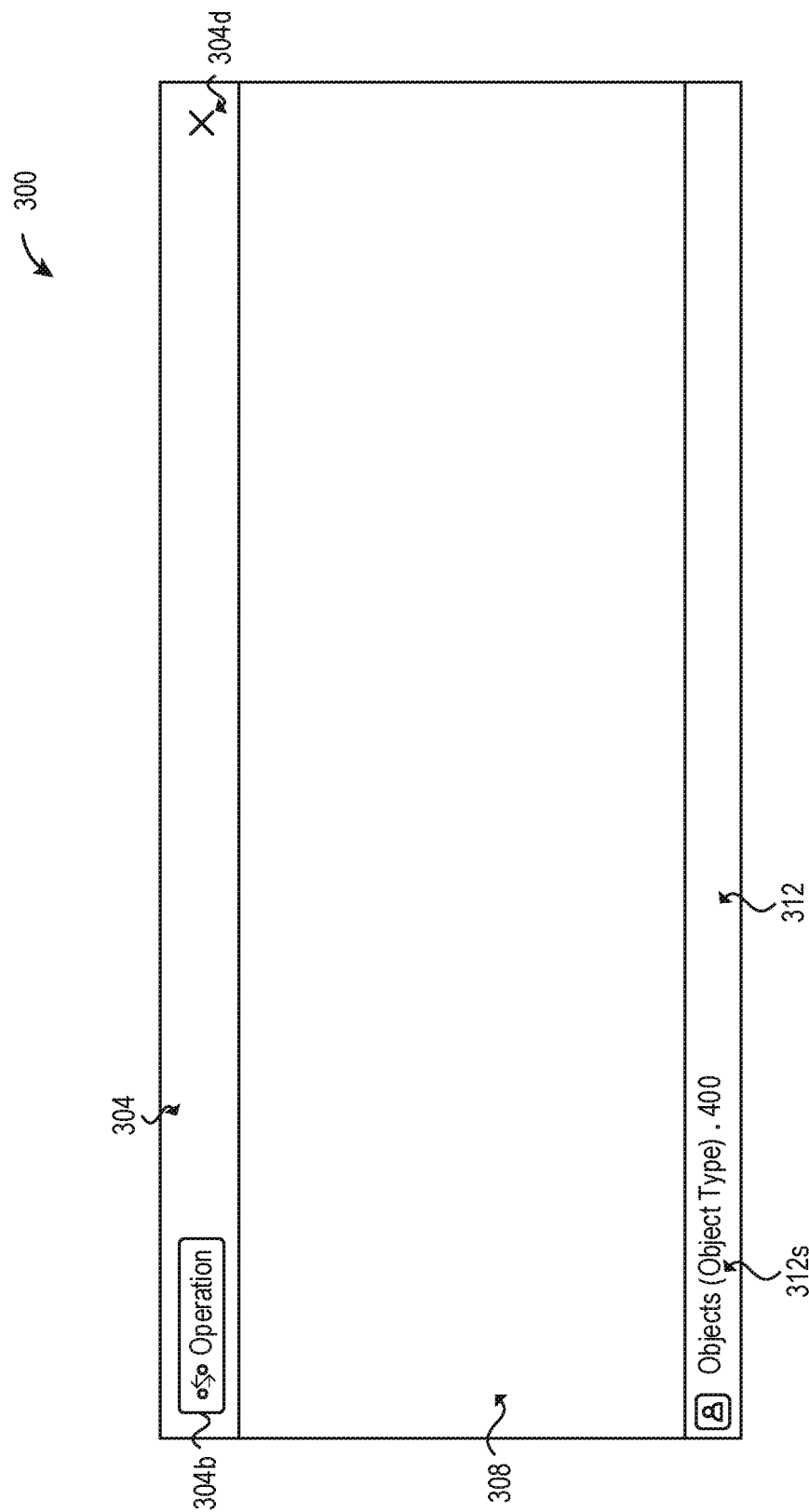
FIG. 3 illustrates an example operation board.

An operation board can include a board header, a board body, and a board footer. FIG. 3 shows an example operation board 300 of a generic board type with a board header 304, a board body 308, and a board footer 312. A generic operation board can be extended by operations such as the filter operation, the switch operation, and the enrich operation. A board header can explain what the board is, and visually describe the input and operation. The board header illustrated in FIG. 3 includes a board type badge 304b and a delete board input element 304d (e.g., a button). A board body 308 can show the internal logic of an operation corresponding to or representing by the board and allow a user control a board. For example, a board body can include internal logic of an operation, such as properties, configurations, buttons, and lines. A board body can be a blank canvas and accept information and limitations (e.g., a person age is within a certain range) added to the board body. A board footer can show a summary of the object type represented by the operation board (such as the input object type, the output object type, and/or any object type internal to the operation board) containing the board footer. The board footer 312 illustrated in FIG. 3 includes a summary 312s of a count of the objects of the object type represented by the operation board 300. The input of an operation board can be the output (e.g., a set of objects of an object type, whether the object type is part of an ontology) of the preceding (e.g., immediate preceding) board. The output of an operation board can be a set of objects of an object type, such as a constrained, enriched, or pivoted object set.

Figure 4A:
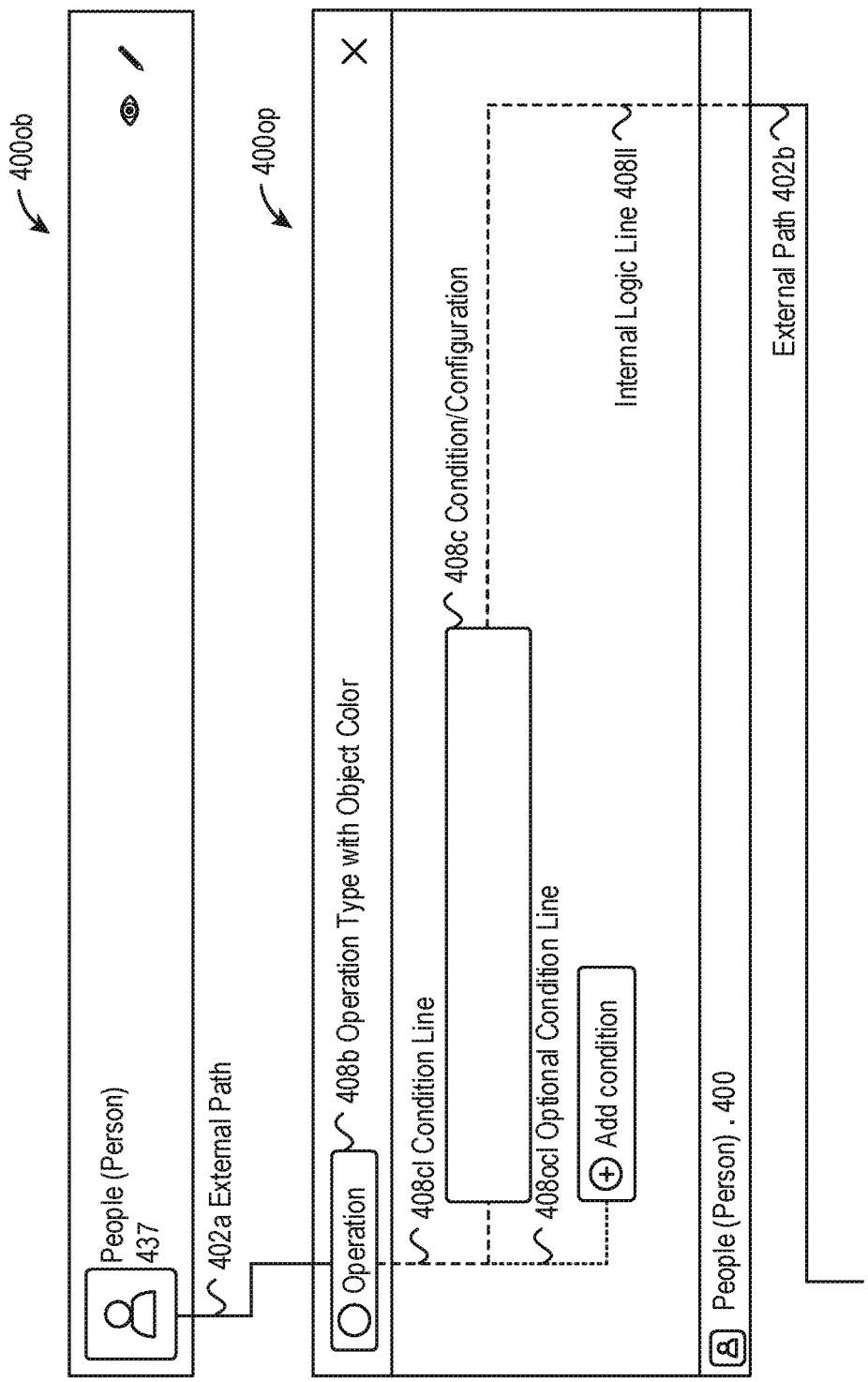
FIGS. 4A-4D show an example configuration of an object board linked to an operation board.
Figure 4B:
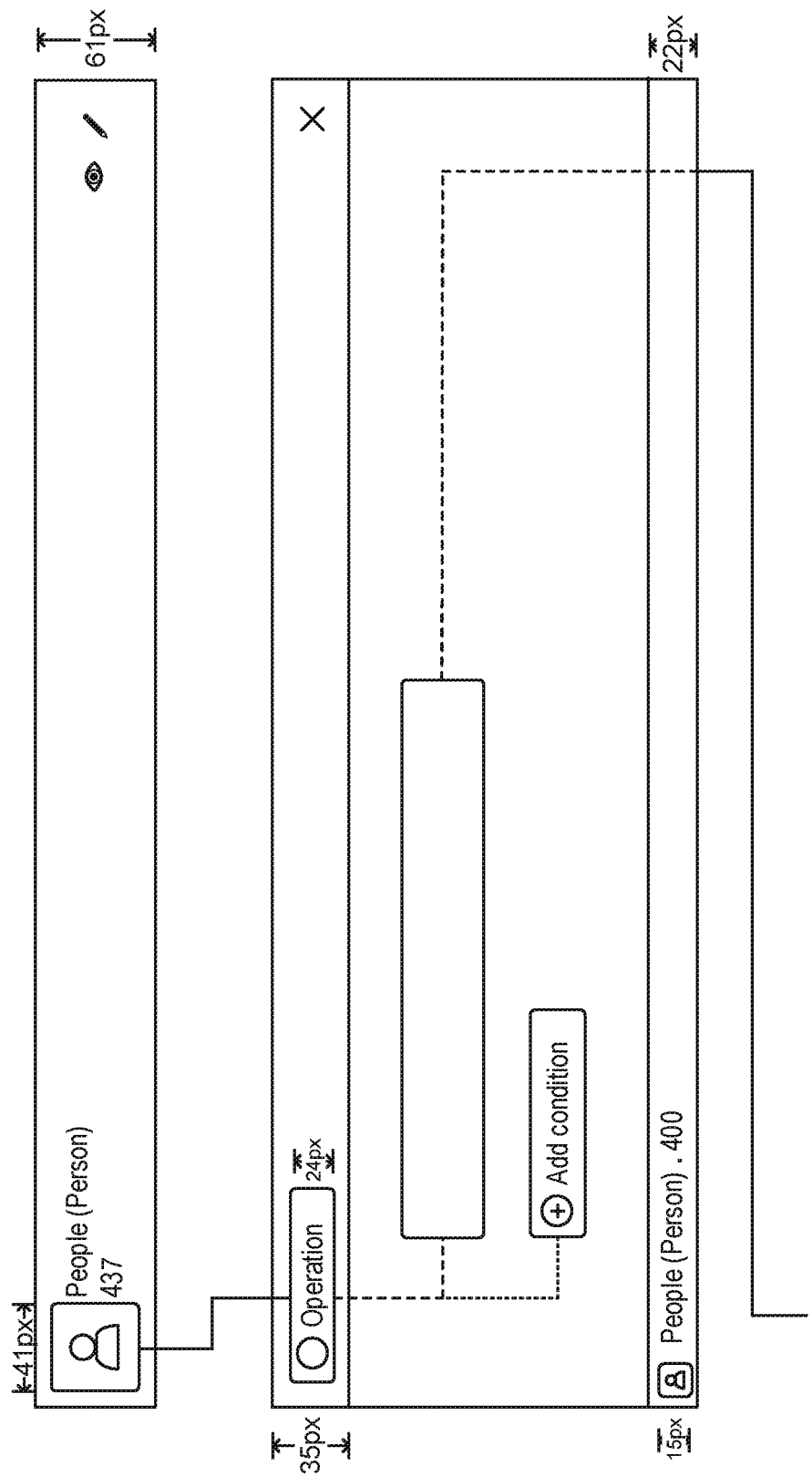
Figure 4C:
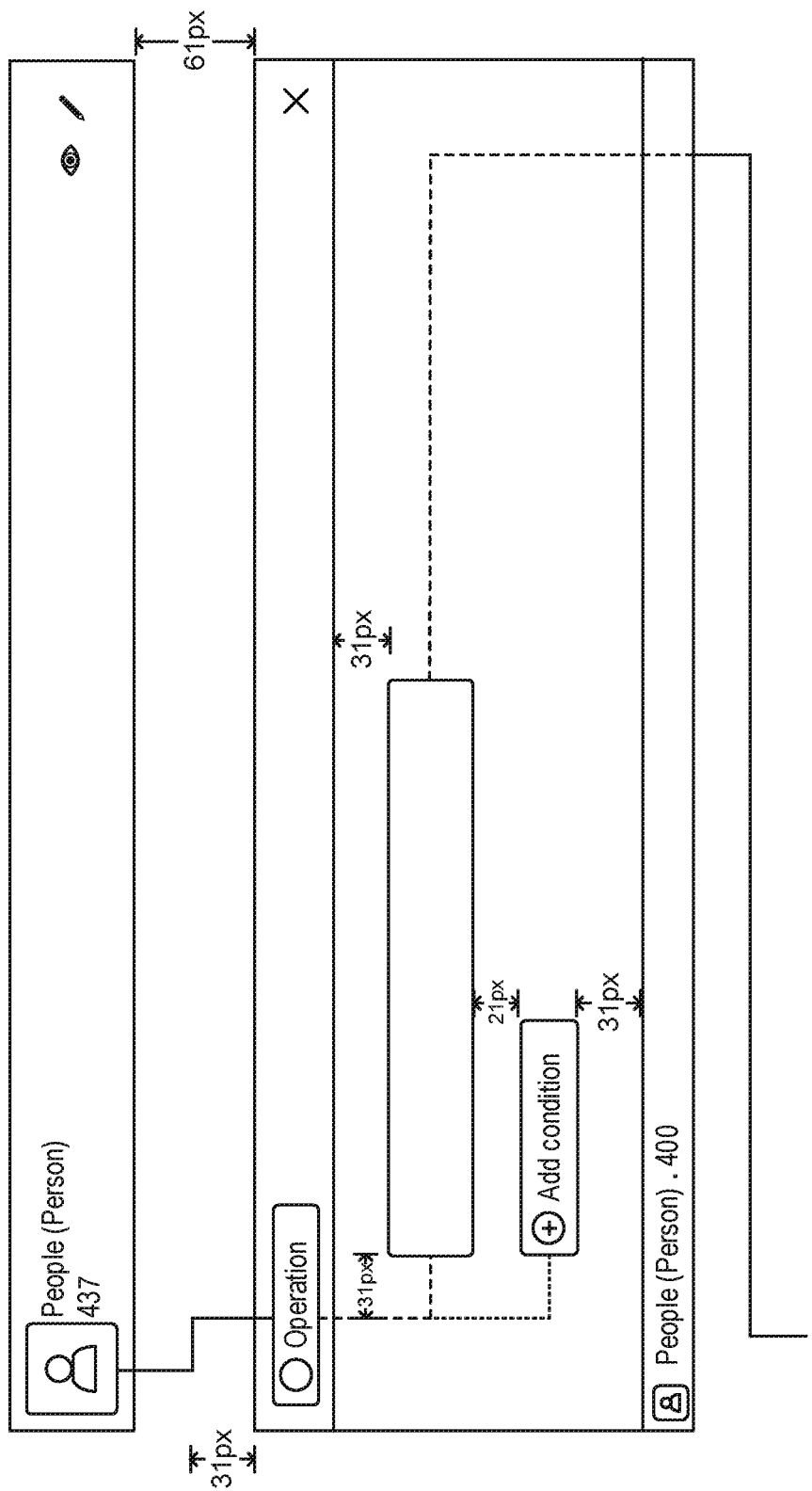
Figure 4D:
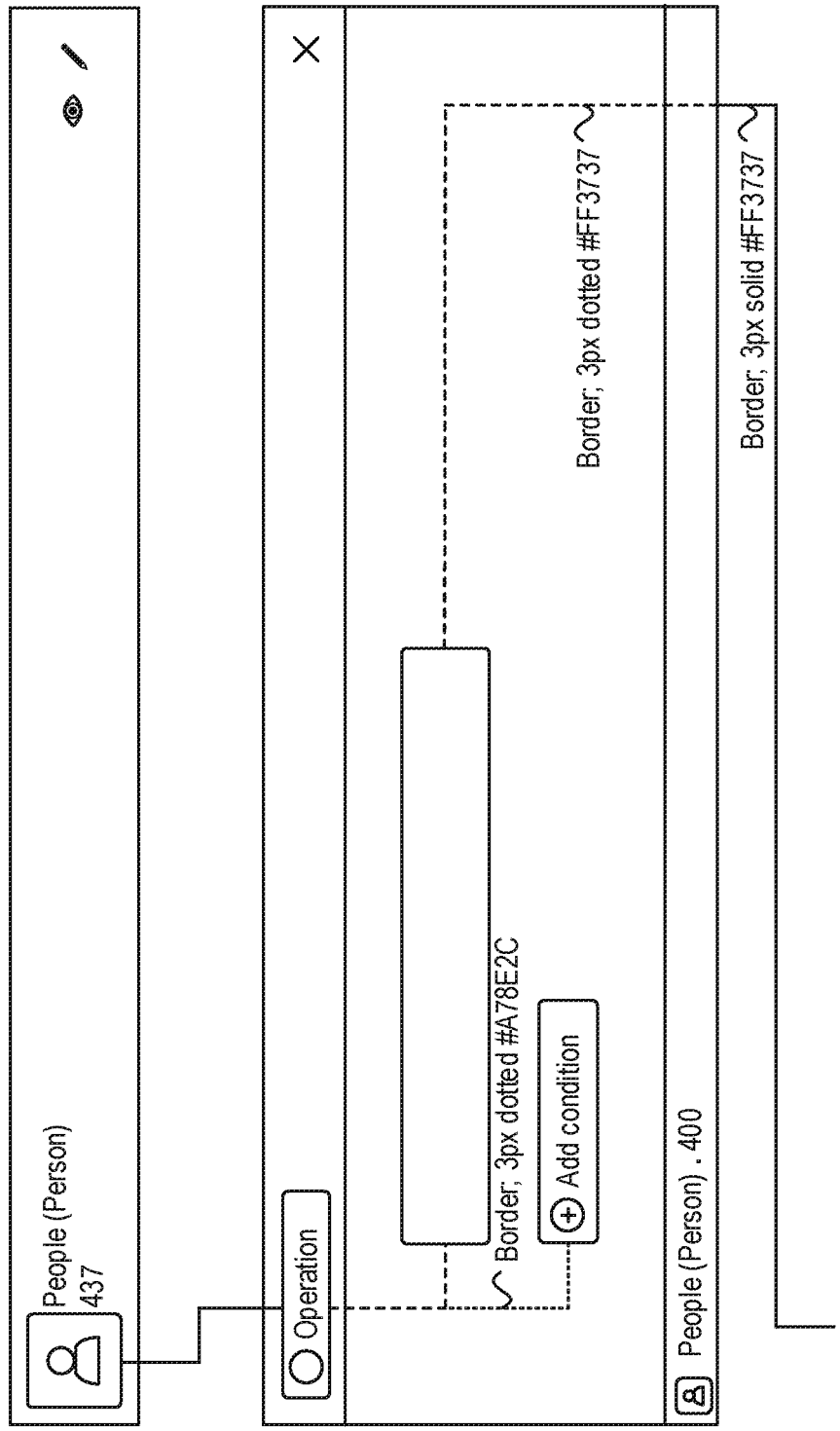

FIGS. 4A-4D show an example configuration of an object board of the person object type linked to an operation board (such as a filter operation board, a switch operation board, and an enrich operation board). In FIG. 4A, the person object board 400ob is connected to the operation board 400op via an external path 402a with respect to the person object board 400ob and the operation board 400op. The operation board 400op is shown to be connected to the next board (e.g., an operation board) via an external path 402b. The header of the operation board 400 can have a board badge 404b indicating the operation type represented by the operation board 400ob. The color of the board badge 404b can be a color specific to the input object type of the operation board 400op. The body of the operation board can include one or more conditions or configurations, such as the condition represented by a condition element 408c. The condition element 412 can be connected to the person object board 400ob via a condition line or path 408cl. The condition element 412 can be connected via an internal logic line or path 408ll and the external path 402b to the next board. The body of the operation board 400 can include an optional condition line 408ocl connected to the condition line 408cl and an input element 408ie (e.g., a button, such as an add condition button). After a user selects the input element 408ie (e.g., by pressing the add condition button), an additional condition element can be shown in the body of the operation board next to (e.g., below) the other condition element 408c. FIGS. 4B-4D show example spacing and colors of internal and external lines or paths of the operation board 400op.

Figure 5:
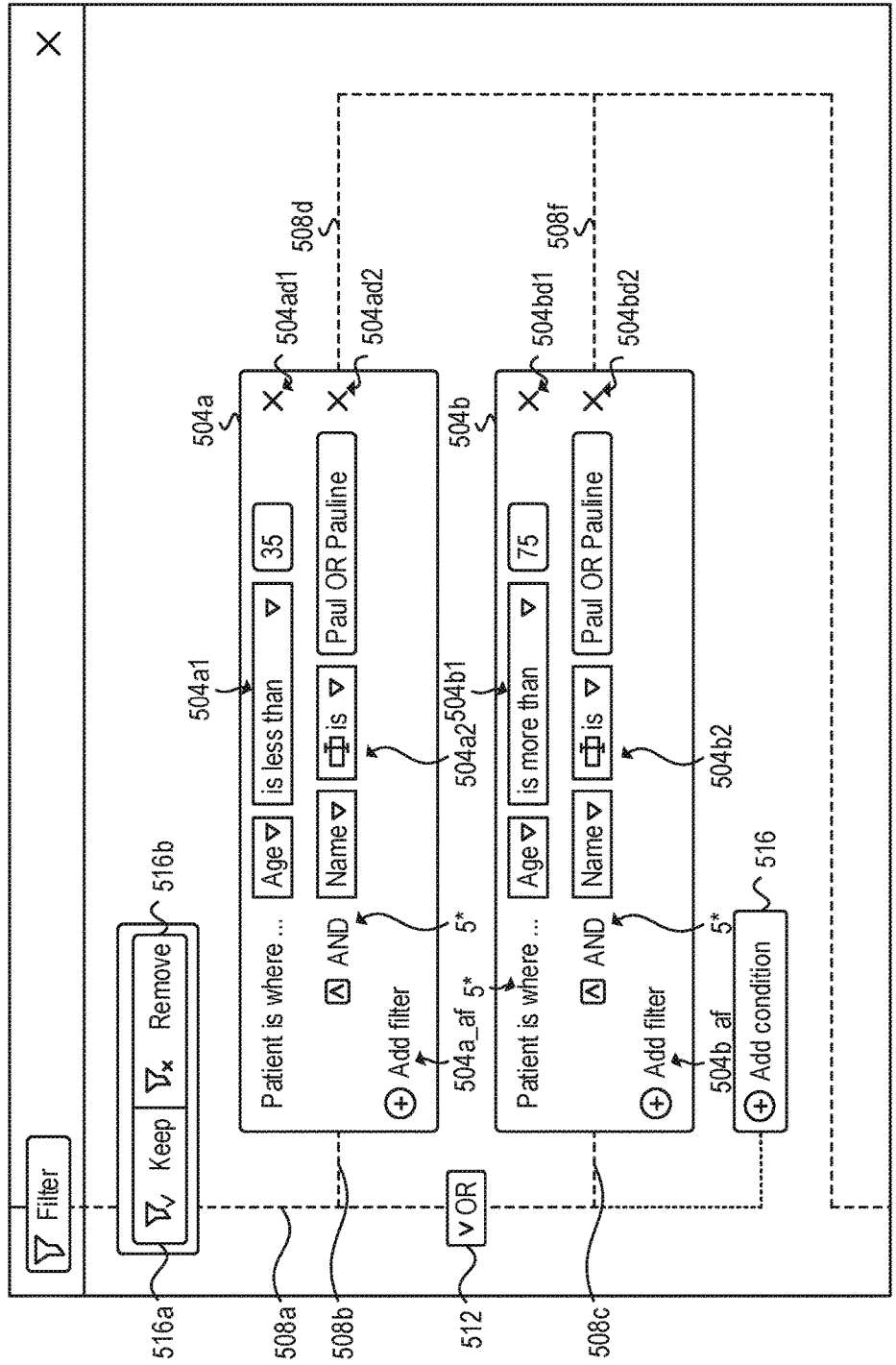
FIG. 5 illustrates an example filter operation board.

FIG. 5 illustrates an example filter operation board. The filter operation board 500 illustrated in FIG. 5 can comprise one or more condition or filter elements 504a, 504b connected, via one or more intra-filter operation board paths 508a-508f, by one or more logic operations 512 (e.g., and, or, xor logic operations). The condition or filter elements 504a, 504b can represent conditions or filters. The filter operation board can include input elements 516a, 516b (e.g., buttons), for keeping or removing matches or satisfies the conditions or filters represented by the condition or filter elements 504a, 504b in the filter operation board 500. Condition or filter elements 504a, 504b can be connected by a logic operation 512 (an "or" logic operation shown). Each condition or filter element can include one or more (sub-) condition or filter elements. Two sub-condition or filter elements can be connected by an "and" logic operation as illustrated in FIG. 5. A condition or filter element and a (sub-)condition or filter element can include a property name, a comparison operator, and a value for comparison. FIG. 5 shows that the condition or filter element 504a includes two (sub)condition or filter elements 504a1, 504a2, each with a property name ("age" and "name property" names shown), a comparison operation ("is less than" and "is" operations shown), and a value for comparison ("35" and "Paul OR Pauline" values for comparison shown). Each (sub-)condition or filter element can include a delete input element (e.g., a button) 504ad1, 504ad2, 504bd1, 504bd2. An additional (sub-) condition or filter element can be added by, for example, selecting the "Add filter" 504a_af, 504b_af input element (e.g., pressing an icon or associated descriptive text, such as "Add filter"). An additional condition or filter element can be added by, for example, select (e.g., press) an input element 516 (e.g., a button). The output of the filter object board 500 can be the input objects constrained by the internal logic of the board. The input type of the filter operation board and the output type of the filter operation board can identical (e.g., the patient object type). The output of the filter object board can include the same number or fewer number of objects compared to the number of objects that input of the object board has. The output of a filter operation board can be, for example, a set of patients satisfying certain criteria.

Figure 6:
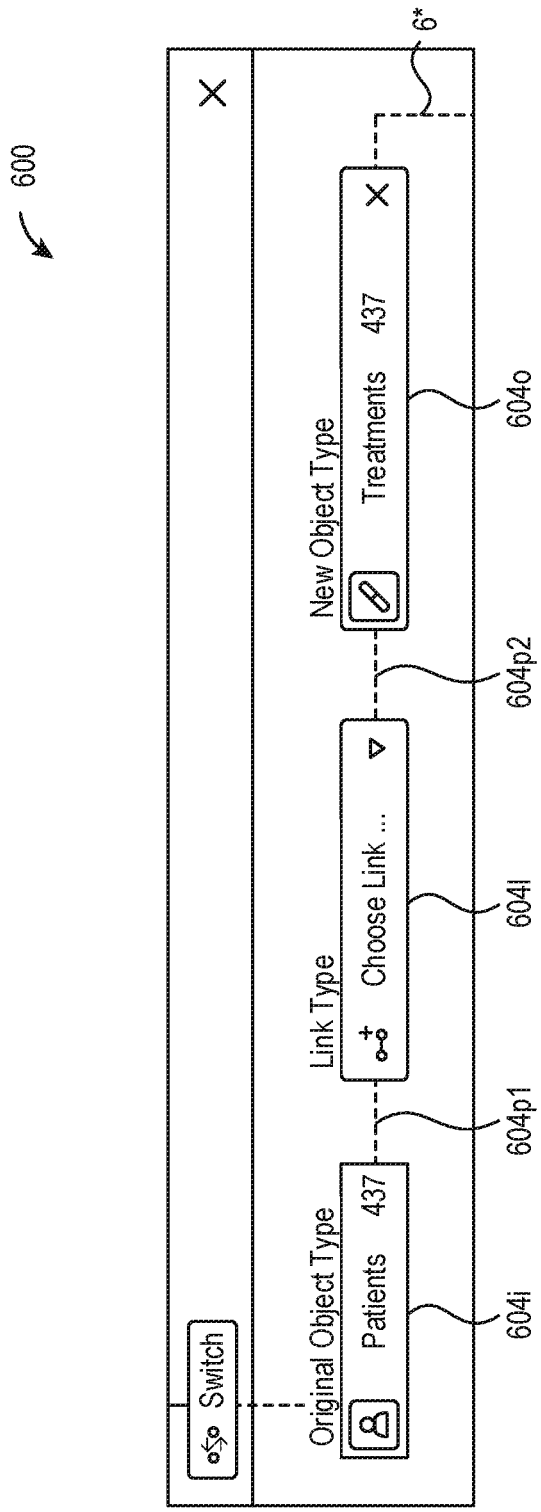
FIG. 6 illustrates an example switch operation board.

FIG. 6 illustrates an example switch operation board. The switch operation board 600 illustrated in FIG. 6 includes (i) a first switch element 604i representing the input object type of the switch operation board 600. The switch operation board 600 includes (ii) a second switch element 604o representing the output object type of the switch operation board 600. The colors of the switch elements 604i, 604o or portions thereof (e.g., icons in the switch elements 604i, 604o) can be the colors assigned to or used by the object types represented by the switch elements 604i, 604o. The first switch element and the second switch element 604i, 604o can be connected by a switch link element 604l, via an intra-switch operation board path 604p1, 604p2, representing a switch relationship between the input object type of the switch operation board and the output object type of the switch operation board. The original or input object type of the switch operation board 600 can be inherited from previous (e.g., immediately preceding) object or operation board and be immutable. The link represented by the switch link element 604l can be a relationship between the two object types 604i, 604o. The new or output object type of the switch operation board can be the object type to enrich the original or input object type. The new or output object type of the switch operation board can be the object type the original or input object type is being pivoted into. The switch operation board 600 can auto-suggest relationships from the ontology via a typeahead dropdown. For example, after a link type is selected, only possible new object types, given the link type and the original or input object type, can be shown to the user. If a user fills out the new object type first, the set of relationships or link types can be constrained based on the ontology. For example, after a new object type is selected, only possible relationships or links types, given the object types, can be shown to the user. If a user fills out the link type first, the set of possible new object types can be constrained based on the ontology. The output of the switch operation board 600 can be a set of objects of the new or output object type of the switch operation board 600. The input of the switch operation board can be a set of patients satisfying one or more certain criteria, and the output of the switch operation board can be the treatments these patients have received. Objects of the new object type can be retrieved from a database.

Figure 7:
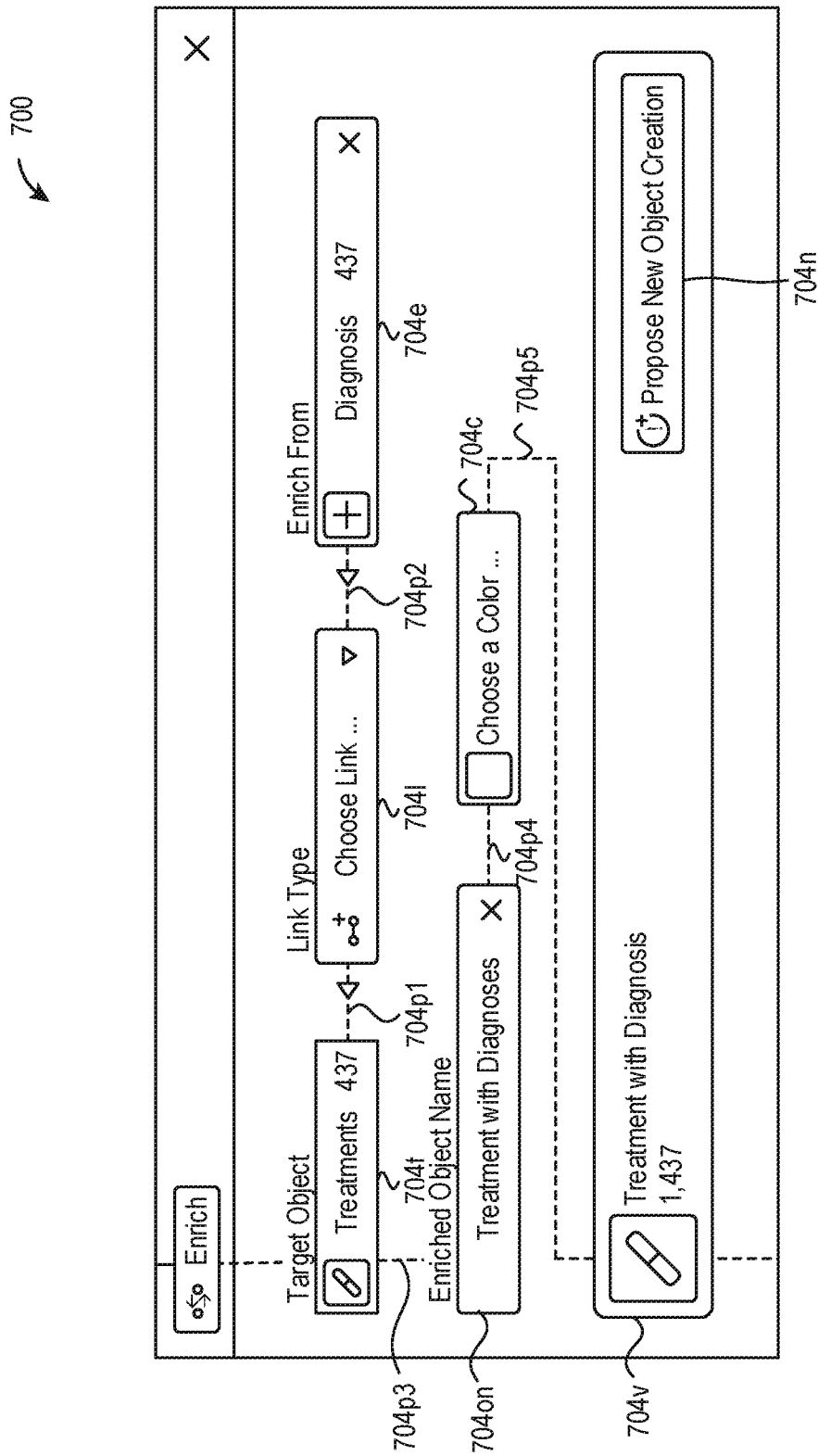
FIG. 7 illustrates an example enrich operation board.

FIG. 7 illustrates an example enrich operation board. The enrich operation board 700 illustrated in FIG. 7 includes (i) a first enrich element 704t representing the input object type of the enrich operation board. The enrich operation board 700 can include (ii) a second enrich element 704e representing a second object type of the ontology. Objects of the second object type can be retrieved from a database (e.g., a database with information related to what treatments should be administered given certain diagnoses). The enrich operation board 700 can include (iii) a third enrich element 704*v* representing the output object type of the enrich operation board, the output object type of the enrich operation board comprising a mutated or virtual object type representing a combination of the input object type of the enrich operation board and the second object type. The first enrich element 704*t* and the second enrich element 704*e* are connected, via a first intra-enrich operation board path 704*p*1, 704*p*2, by an enriching link element 704*l* representing an enrich relationship between the input object type of the enrich operation board 700 and the output object type of the enrich operation board 700. The first enrich element 704*t* can be connected, via a second intra-enrich operation board path 704*p*3, 704*p*4, 704*p*5, to the third enrich element 704*v*. The user can input the name of the mutated or virtual object type and assign a color to the mutated or virtual object type using input elements 704*on*, 704*c* (e.g., a text box or a drop down menu). The original or input object type of the enrich operation board 700 can be inherited from previous board and be immutable. The object to enrich from can be an object type from the ontology. A mutated or virtual object type can be an object type that is not (yet) part of the ontology. The output of the enrich operation board can include (e.g., by merging) properties (e.g., columns) from both the two object types represented by the enrich elements 704*t*, 704*e* that match the criterion represented by the enriching link element 704*l*. As illustrated in FIG. 7, the enrich operation board 700 can include an input element (e.g., a button) 704*n* that user can use to propose a new object type. The output of the switch operation board can be the diagnoses that the patients may have given the treatments the patients have received.

Figure 8:
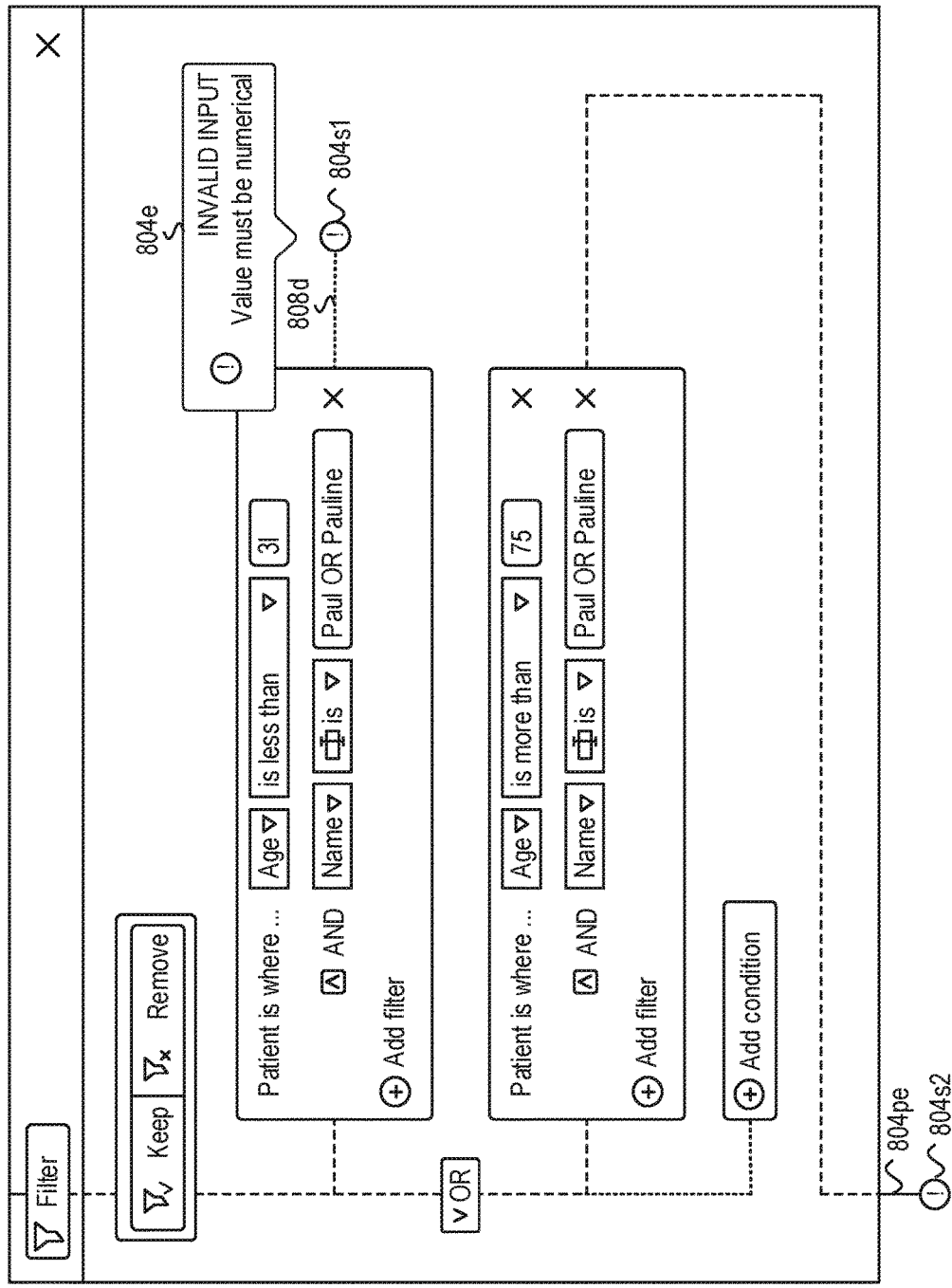
FIG. 8 illustrates an example filter operation board showing an error message.

When there is an error in an operation board, the internal path of the board related to the error can be directly cut with an error message shown. The external path of the operation board can also be cut. FIG. 8 illustrates an example filter operation board showing an error message. The filter operation board 800 in FIG. 8 includes an error message 804*e* and an error sign 804*s*1, indicating an invalid input for one of the (sub-)condition or filter element. The path 808*d* after the (sub-)condition or filter element has been cut (compared to the path 508*d* in FIG. 5) by the error sign 804*s*1. The external path 800*pe* of the operation board 800 is shown to be cut by another error sign 804*s*2.

Data Analysis Method

Figure 9:
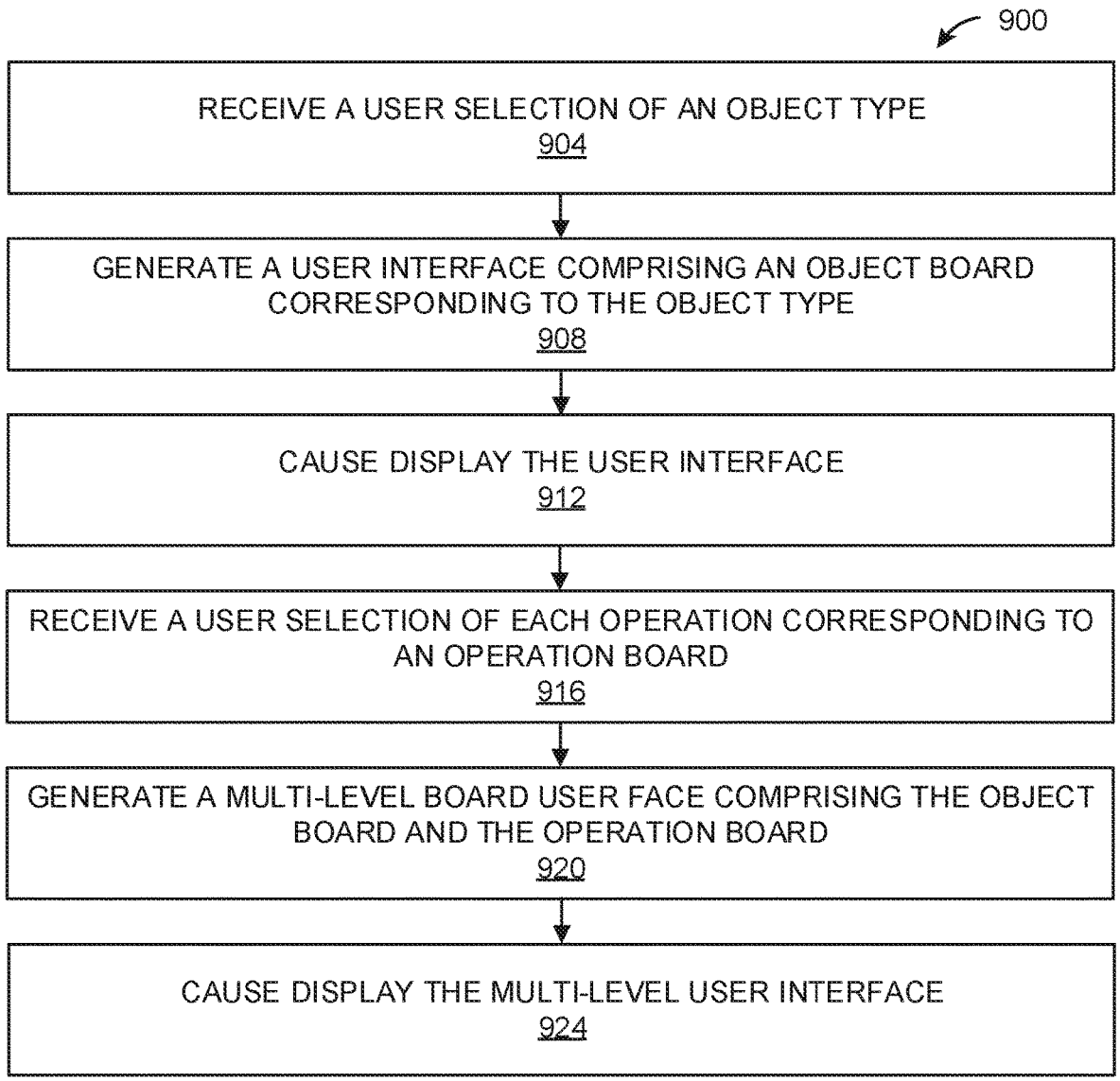
FIG. 9 is a flow diagram showing an example process of generating a user interface for performing data analysis (e.g., high-scale top-down data analysis).

FIG. 9 is a flow diagram showing an example method 900 for data analysis (e.g., for performing high-scale top-down data analysis and/or generating a user interface for performing high-scale top-down data analysis), according to various embodiments of the present disclosure. The method 900 can be implemented in various environments and computer systems, including, for example, the computer system 1000 of FIG. 10. The operations of method 900 presented below are intended to be illustrative. Depending on the implementation, the example method 900 can include additional, fewer, or alternative steps performed in various orders or in parallel. The example method 900 can be implemented in various computing systems or devices including one or more processors.

At block 904, a computer system (e.g., the computer system 1000 of FIG. 10) can receiving a user selection of a first object type of a plurality of object types. For example, the computer system can receive the user selection using the user interface 100*a* described with reference to FIG. 1A. The plurality of object types can comprise a patient object type, a treatment object type, and a diagnosis object type. The plurality of object types can be part of an ontology.

At block 908, the computer system can generate an initial user interface (e.g., the user interface 100*b* described with reference to FIG. 1B) comprising an object board (e.g., the patient object boards 10010, 200 described with reference to FIGS. 1 and 2, respectively) at a first display level. The object board can correspond to the first object type of the plurality of object types. The object board can comprise an object board body. In some embodiments, the initial user interface comprises (i) the object board at the first display level connected to (ii) a plurality of selection elements at a second display level. The plurality of selection elements can correspond to the plurality of operations. In some embodiments, the computer system can retrieve data associated with objects of the first object type (e.g., patient data for a plurality of patients) from one or more databases.

At block 912, the computer system can cause display the user interface

At block 916, the computer system can receive a user selection of each of a plurality of operations corresponding to a plurality of operation boards.

At block 920, the computer system can generate a multi-level board user interface (e.g., the user interfaces 100*c*, 100*d* described with reference to FIGS. 1C-1D). The multi-level board user interface can comprise a plurality of boards at different display levels. The plurality of boards can comprise (i) the object board at the first display level and (ii) a plurality of operation boards each at a different second display level. In some embodiments, each of the plurality of operation boards comprises an operation board header, an operation board body, and an operation board footer. The multi-level board user interface can comprise the object board and operation boards of the plurality of operation boards that are arranged vertically, horizontally, or a combination thereof. In some embodiments, an input object type of the first operation board comprises the first object type. An output object type of each of the plurality of operation boards can be an input object type of the next operation board.

In some embodiments, the object board is connected, via a first inter-board path (e.g., the path 128_01 in FIG. 1C), to a first operation board of the plurality of operation boards. Each of the plurality of operation boards, other than a last operation board, can be connected, via a second inter-board path (e.g., the paths 128_12, 128_23 in FIG. 1D), to a next operation board of the plurality of operation boards.

In some embodiments, the plurality of operation boards can correspond to a plurality of operations. For example, the plurality of operations can comprise a filter operation, a switch operation, and an enrich operation. The plurality of operations can be part of the ontology. The plurality of operation boards can comprise a filter operation board (e.g., an enrich operation board, and a switch operation board.

In some embodiments, the filter operation board (e.g., the filter operation board 500 described with reference to FIG. 5) can comprise one or more filter elements connected, via one or more intra-filter operation board paths, by one or more logic operations. The input type of the filter operation board and the output type of the filter operation board can identical.

In some embodiments, the switch operation board (e.g., the switch operation board 600 described with reference to FIG. 6) can comprise (i) a first switch element representing the input object type of the switch operation board and (ii) a second switch element representing the output object type of the switch operation board. The first switch element and the second switch element can be connected by a switch link element, via an intra-switch operation board path, representing a switch relationship between the input object type of the switch operation board and the output object type of the switch operation board.

In some embodiments, the computer system can receive a user selection of the output object type of the switch operation board. The computer system can determine a plurality of switch relationships compatible with the input object type of the switch operation board and the output object type of the switch operation board. The computer system can receive a user selection of the switch relationship of the plurality of switch relationships.

In some embodiments, the enrich operation board (e.g., the enrich operation board 700 described with reference to FIG. 7) comprises (i) a first enrich element representing the input object type of the enrich operation board, (ii) a second enrich element representing a second object type of the plurality of object types, or a combination thereof, and (iii) a third enrich element representing the output object type of the enrich operation board, the output object type of the enrich operation board comprising a virtual object type representing a combination of the input object type of the enrich operation board and the second object type. In some embodiments, the first enrich element and the second enrich element are connected, via a first intra-enrich operation board path, by an enriching link element representing an enrich relationship between the input object type of the enrich operation board and the output object type of the enrich operation board. In some embodiments, the first enrich element is connected, via a second intra-enrich operation board path, to the third enrich element. In some embodiments, the computer system can add the output object type of the enrich operation comprising the virtual object type to the plurality of object types. The output object type of the enrich operation then becomes part of the ontology.

In some embodiments, the computer system can receive a user selection of the enrich relationship. The computer system can determine a plurality of second object types compatible with the input object type of the enrich operation board and the enrich relationship. The computer system can receive a user selection of the second object type of the plurality of second object types.

In some embodiments, the plurality of objects, the plurality of operations and the inter-board paths represent an ontology. In some embodiments, the plurality of objects, the plurality of operations, the inter-board paths, and the intra-board paths represent an ontology. In some embodiments, a combination of the inter-board paths and the intra-board paths represent a path from the first object type to the output object type of a last board of the plurality of boards. The boards and paths can be analogous to a circuit diagram.

In some embodiments, the computer system can receive an invalid user input with respect to a first element in an operation board of the plurality of operation boards. The computer system can generate an error user interface (e.g., the interface 800 described with reference to FIG. 8) comprising an error message adjacent to, or overlapping, the first element in the operation board. The first element of the operation board may not be connected to a second element in the operation board, via a first intra-board path of the operation board and/or a next operation board of the operation board, via a second intra-board path of the operation board.

In some embodiments, the computer system can retrieve patient data for a plurality of patients, treatment data of the plurality of patients, and diagnosis information associated with the treatment data from one or more databases. The computer system can generate the multi-level board user interface using the patient data, the treatment data, and the diagnosis information.

At block 924, the computer system can cause display the multi-level board user interface. The computer system can generate a template comprising relationships between and within the object board and the plurality of operation boards. In some embodiments, the computer system can generate an output file comprising (i) relationships between and within the object board and the plurality of operation boards and (ii) data associated with the patient object type, the retreatment object type, and the diagnosis object type. The output file can then be distributed and/or published.

Hardware Implementation

The techniques described herein are implemented by one or more special-purpose computing devices. The special-purpose computing devices may be hard-wired to perform the techniques, or may include circuitry or digital electronic devices such as one or more application-specific integrated circuits (ASICs) or field programmable gate arrays (FPGAs) that are persistently programmed to perform the techniques, or may include one or more hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, server computer systems, portable computer systems, handheld devices, networking devices or any other device or combination of devices that incorporate hard-wired and/or program logic to implement the techniques.

Computing device(s) are generally controlled and coordinated by operating system software, such as iOS, Android, Chrome OS, Windows XP, Windows Vista, Windows 7, Windows 8, Windows Server, Windows CE, Unix, Linux, SunOS, Solaris, iOS, Blackberry OS, VxWorks, or other compatible operating systems. In other embodiments, the computing device may be controlled by a proprietary operating system. Conventional operating systems control and schedule computer processes for execution, perform memory management, provide file system, networking, I/O services, and provide a user interface functionality, such as a graphical user interface ("GUI"), among other things.

Figure 10:
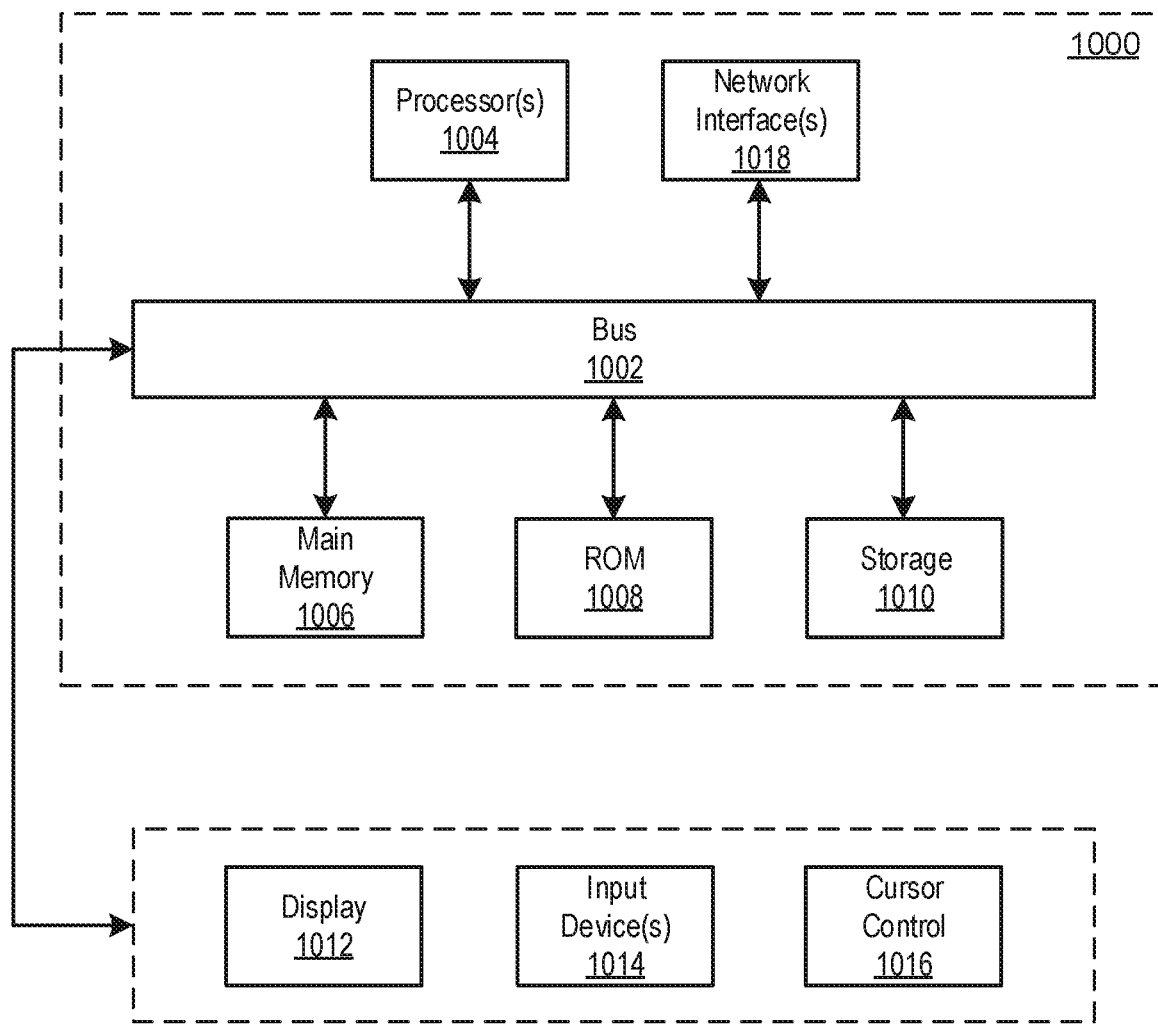
FIG. 10 illustrates a block diagram of an example computer system in which any of the embodiments described herein can be implemented.

FIG. 10 is a block diagram that illustrates a computer system 1000 upon which any of the embodiments described herein may be implemented. The computer system 1000 includes a bus 1002 or other communication mechanism for communicating information, one or more hardware processor 1004 coupled with bus 1002 for processing information. Hardware processor 1004 or processors may be, for example, one or more general purpose microprocessors.

The computer system 1000 also includes a main memory 1006, such as a random-access memory (RAM), cache and/or other dynamic storage devices, coupled to bus 1002 for storing information and instructions to be executed by processor 1004. Main memory 1006 also may be used for storing temporary variables or other intermediate information during execution of instructions to be executed by processor 1004. Such instructions, when stored in storage media accessible to processor 1004, render computer system 1000 into a special-purpose machine that is customized to perform the operations specified in the instructions.

The computer system 1000 further includes a read only memory (ROM) 1008 or other static storage device coupled to bus 1002 for storing static information and instructions for processor 1004. A storage device 1010, such as a magnetic disk, optical disk, or USB thumb drive (Flash drive), etc., is provided and coupled to bus 1002 for storing information and instructions.

The computer system 1000 may be coupled via bus 1002 to a display 1012, such as a cathode ray tube (CRT) or LCD display (or touch screen), for displaying information to a computer user. An input device 1014, including alphanumeric and other keys, is coupled to bus 1002 for communicating information and command selections to processor 1004. Another type of user input device is cursor control 1016, such as a mouse, a trackball, or cursor direction keys for communicating direction information and command selections to processor 1004 and for controlling cursor movement on display 1012. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen lacking a cursor.

The computing system 1000 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules but may be represented in hardware or firmware. Generally, the modules described herein refer to logical modules that may be combined with other modules or divided into sub-modules despite their physical organization or storage.

The computer system 1000 may implement the techniques described herein using customized hard-wired logic, one or more ASICs or FPGAs, firmware and/or program logic which in combination with the computer system causes or programs computer system 1000 to be a special-purpose machine. According to one embodiment, the techniques herein are performed by computer system 1000 in response to processor(s) 1004 executing one or more sequences of one or more instructions contained in main memory 1006. Such instructions may be read into main memory 1006 from another storage medium, such as storage device 1010. Execution of the sequences of instructions contained in main memory 1006 causes processor(s) 1004 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 1010. Volatile media includes dynamic memory, such as main memory 1006. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 1002. Transmission media can also take the form of acoustic or light waves, such as those generated during radio-wave and infra-red data communications.

Various forms of media may be involved in carrying one or more sequences of one or more instructions to processor 1004 for execution. For example, the instructions may initially be carried on a magnetic disk or solid-state drive of a remote computer. The remote computer can load the instructions into its dynamic memory and send the instructions over a telephone line using a modem. A modem local to computer system 1000 can receive the data on the telephone line and use an infra-red transmitter to convert the data to an infra-red signal. An infra-red detector can receive the data carried in the infra-red signal and appropriate circuitry can place the data on bus 1002. Bus 102 carries the data to main memory 1006, from which processor 1004 retrieves and executes the instructions. The instructions received by main memory 1006 may retrieves and executes the instructions. The instructions received by main memory 1006 may optionally be stored on storage device 1010 either before or after execution by processor 1004.

The computer system 1000 also includes a communication interface 1018 coupled to bus 1002. Communication interface 1018 provides a two-way data communication coupling to one or more network links that are connected to one or more local networks. For example, communication interface 1018 may be an integrated service digital network (ISDN) card, cable modem, satellite modem, or a modem to provide a data communication connection to a corresponding type of telephone line. As another example, communication interface 1018 may be a local area network (LAN) card to provide a data communication connection to a compatible LAN (or WAN component to communicated with a WAN). Wireless links may also be implemented. In any such implementation, communication interface 1018 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world-wide packet data communication network now commonly referred to as the "Internet". Local network and Internet both use electrical, electromagnetic or optical signals that carry digital data streams. The signals through the various networks and the signals on network link and through communication interface 1018, which carry the digital data to and from computer system 1000, are example forms of transmission media.

The computer system 1000 can send messages and receive data, including program code, through the network (s), network link and communication interface 1018. In the Internet example, a server might transmit a requested code for an application program through the Internet, the ISP, the local network and the communication interface 1018.

The received code may be executed by processor 1004 as it is received, and/or stored in storage device 1010, or other non-volatile storage for later execution.

Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry.

The various features and processes described above may be used independently of one another or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

Engines, Components, and Logic

Certain embodiments are described herein as including logic or a number of components, engines, or mechanisms. Engines may constitute either software engines (e.g., code embodied on a machine-readable medium) or hardware engines. A "hardware engine" is a tangible unit capable of performing certain operations and may be configured or arranged in a certain physical manner. In various example embodiments, one or more computer systems (e.g., a standalone computer system, a client computer system, or a server computer system) or one or more hardware engines of a computer system (e.g., a processor or a group of processors) may be configured by software (e.g., an application or application portion) as a hardware engine that operates to perform certain operations as described herein.

In some embodiments, a hardware engine may be implemented mechanically, electronically, or any suitable combination thereof. For example, a hardware engine may include dedicated circuitry or logic that is permanently configured to perform certain operations. For example, a hardware engine may be a special-purpose processor, such as a Field-Programmable Gate Array (FPGA) or an Application Specific Integrated Circuit (ASIC). A hardware engine may also include programmable logic or circuitry that is temporarily configured by software to perform certain operations. For example, a hardware engine may include software executed by a general-purpose processor or other programmable processor. Once configured by such software, hardware engines become specific machines (or specific components of a machine) uniquely tailored to perform the configured functions and are no longer general-purpose processors. It will be appreciated that the decision to implement a hardware engine mechanically, in dedicated and permanently configured circuitry, or in temporarily configured circuitry (e.g., configured by software) may be driven by cost and time considerations.

Accordingly, the phrase "hardware engine" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented engine" refers to a hardware engine. Considering embodiments in which hardware engines are temporarily configured (e.g., programmed), each of the hardware engines need not be configured or instantiated at any one instance in time. For example, where a hardware engine comprises a general-purpose processor configured by software to become a special-purpose processor, the general-purpose processor may be configured as respectively different special-purpose processors (e.g., comprising different hardware engines) at different times. Software accordingly configures a particular processor or processors, for example, to constitute a particular hardware engine at one instance of time and to constitute a different hardware engine at a different instance of time.

Hardware engines can provide information to, and receive information from, other hardware engines. Accordingly, the described hardware engines may be regarded as being communicatively coupled. Where multiple hardware engines exist contemporaneously, communications may be achieved through signal transmission (e.g., over appropriate circuits and buses) between or among two or more of the hardware engines. In embodiments in which multiple hardware engines are configured or instantiated at different times, communications between such hardware engines may be achieved, for example, through the storage and retrieval of information in memory structures to which the multiple hardware engines have access. For example, one hardware engine may perform an operation and store the output of that operation in a memory device to which it is communicatively coupled. A further hardware engine may then, at a later time, access the memory device to retrieve and process the stored output. Hardware engines may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented engines that operate to perform one or more operations or functions described herein. As used herein, "processor-implemented engine" refers to a hardware engine implemented using one or more processors.

Similarly, the methods described herein may be at least partially processor-implemented, with a particular processor or processors being an example of hardware. For example, at least some of the operations of a method may be performed by one or more processors or processor-implemented engines. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine, but deployed across a number of machines. In some example embodiments, the processors or processor-implemented engines may be located in a single geographic location (e.g., within a home environment, an office environment, or a server farm). In other example embodiments, the processors or processor-implemented engines may be distributed across a number of geographic locations.

Language

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the subject matter has been described with reference to specific example embodiments, various modifications and changes may be made to these embodiments without departing from the broader scope of embodiments of the present disclosure. Such embodiments of the subject matter may be referred to herein, individually or collectively, by the term "invention" merely for convenience and without intending to voluntarily limit the scope of this application to any single disclosure or concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

It will be appreciated that an "engine," "system," "data store," and/or "database" may comprise software, hardware, firmware, and/or circuitry. In one example, one or more software programs comprising instructions capable of being executable by a processor may perform one or more of the functions of the engines, data stores, databases, or systems described herein. In another example, circuitry may perform the same or similar functions. Alternative embodiments may comprise more, less, or functionally equivalent engines, systems, data stores, or databases, and still be within the scope of present embodiments. For example, the functionality of the various systems, engines, data stores, and/or databases may be combined or divided differently.

"Open source" software is defined herein to be source code that allows distribution as source code as well as compiled form, with a well-publicized and indexed means of obtaining the source, optionally with a license that allows modifications and derived works.

The data stores described herein may be any suitable structure (e.g., an active database, a relational database, a self-referential database, a table, a matrix, an array, a flat file, a documented-oriented storage system, a non-relational No-SQL system, and the like), and may be cloud-based or otherwise.

As used herein, the term "or" may be construed in either an inclusive or exclusive sense. Moreover, plural instances may be provided for resources, operations, or structures described herein as a single instance. Additionally, boundaries between various resources, operations, engines, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Although the invention has been described in detail for the purpose of illustration based on what is currently considered to be the most practical and preferred implementations, it is to be understood that such detail is solely for that purpose and that the invention is not limited to the disclosed implementations, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system comprising:
   one or more processors; and
   memory storing instructions that, when executed by the one or more processors, cause the system to perform:
   generating a multi-level board user interface comprising a plurality of boards at different display levels, the plurality of boards comprising (i) an object board at a first display level and (ii) a plurality of operation boards each at a different second display level,
   wherein the object board corresponds to a first object type of a plurality of object types comprising a patient object type, a treatment object type, and a diagnosis object type,
   wherein the object board is connected, via a first inter-board path, to a first operation board of the plurality of operation boards, wherein each of the plurality of operation boards, other than a last operation board, is connected, via a second inter-board path, to a next operation board of the plurality of operation boards, wherein an input object type of the first operation board comprises the first object type, wherein an output object type of each of the plurality of operation boards is an input object type of the next operation board,
   wherein the plurality of operation boards corresponds to a plurality of operations, wherein the plurality of operations comprises a filter operation, a switch operation, and an enrich operation, wherein the plurality of operation boards comprises a filter operation board, an enrich operation board, and a switch operation board,
   wherein the filter operation board comprises one or more filter elements connected, via one or more intra-filter operation board paths, by one or more logic operations, wherein the input type of the filter operation board and the output type of the filter operation board are identical,
   wherein the switch operation board comprises (i) a first switch element representing the input object type of the switch operation board and (ii) a second switch element representing the output object type of the switch operation, wherein the first switch element and the second switch element are connected by a switch link element, via an intra-switch operation board path, representing a switch relationship between the input object type of the switch operation board and the output object type of the switch operation, and
   wherein the enrich operation board comprises (i) a first enrich element representing the input object type of the enrich operation board, (ii) a second enrich element representing a second object type of the plurality of object types, or a combination thereof, and (iii) a third enrich element representing the output object type of the enrich operation board, the output object type of the enrich operation board comprising a virtual object type representing a combination of the input object type of the enrich operation board and the second object type,
   wherein the first enrich element and the second enrich element are connected, via a first intra-enrich operation board path, by an enriching link element representing an enrich relationship between the input object type of the enrich operation board and the output object type of the enrich operation board, and
   wherein the first enrich element is connected, via a second intra-enrich operation board path, to the third enrich element; and
   displaying the multi-level board user interface.

2. The system of claim 1, wherein:
the object board comprises an object board body; or
each of the plurality of operation boards comprises an operation board header, an operation board body, and an operation board footer.

3. The system of claim 1, wherein the multi-level board user interface comprises the object board and second operation boards of the plurality of operation boards that are arranged vertically.

4. The system of claim 1, wherein the instructions, when executed by the one or more processors, cause the system to perform: receiving a user selection of the first object type.

5. The system of claim 1, wherein the instructions, when executed by the one or more processors, cause the system to perform: receiving a user selection of each of the plurality of operations corresponding to the plurality of operation boards.

6. The system of claim 1, wherein the instructions, when executed by the one or more processors, cause the system to perform:
generating an initial user interface comprising (i) the object board at the first display level connected to (ii) a plurality of selection elements at a second display level, wherein the plurality of selection elements corresponds to the plurality of operations; and provide the initial user interface for display to at least one device.

7. The system of claim 1, wherein the instructions, when executed by the one or more processors, cause the system to perform:
receiving a user selection of the output object type of the switch operation board; determining a plurality of switch relationships compatible with the input object type of the switch operation board and the output object type of the switch operation; and
receiving a user selection of the switch relationship of the plurality of switch relationships.

8. The system of claim 1, wherein the instructions, when executed by the one or more processors, cause the system to perform:
receiving a user selection of the enrich relationship;
determining a plurality of second object types compatible with the input object type of the enrich operation board and the enrich relationship; and
receiving a user selection of the second object type of the plurality of second object types.

9. The system of claim 1, wherein the instructions, when executed by the one or more processors, cause the system to perform:
receiving an invalid user input with respect to a first element in an operation board of the plurality of operation boards;
generating an error user interface comprising an error message adjacent to, or overlapping, the first element in the operation board, wherein the first element of the operation board is not connected to a second element in the operation board, via a first intra-board path of the operation board, and/or a next operation board of the operation board, via a second intra-board path of the operation board; and
causing to display the third user interface.

10. The system of claim 1,
wherein the instructions, when executed by the one or more processors, cause the system to perform: retrieving patient data for a plurality of patients, treatment data of the plurality of patients, and diagnosis information associated with the treatment data, and
wherein generating the multi-level board user interface comprises generating the multi-level board user interface using the patient data, the treatment data, and the diagnosis information.

11. The system of claim 1, wherein the instructions, when executed by the one or more processors, cause the system to perform: adding the output object type of the enrich operation comprising the virtual object type to the plurality of object types.

12. The system of claim 1, wherein the instructions, when executed by the one or more processors, cause the system to perform: generating a template comprising relationships between and within the object board and the plurality of operation boards.

13. The system of claim 1, wherein the instructions, when executed by the one or more processors, cause the system to perform: generating an output file comprising (i) relationships between and within the object board and the plurality of operation boards and (ii) data associated with the patient object type, the retreatment object type, and the diagnosis object type.

14. The system of claim 1, wherein the plurality of objects, the plurality of operations, the inter-board paths, and the intra-board paths represent an ontology.

15. The system of claim 1, wherein a combination of the inter-board paths and the intra-board paths represent a path from the first object type to the output object type of a last board of the plurality of boards.

16. A method comprising:
generating a multi-level board user interface comprising a plurality of boards at different display levels, the plurality of boards comprising (i) an object board at a first display level and (ii) a plurality of operation boards each at a different second display level,
wherein the object board corresponds to a first object type of a plurality of object types comprising a patient object type, a treatment object type, and a diagnosis object type,
wherein the object board is connected, via a first inter-board path, to a first operation board of the plurality of operation boards, wherein each of the plurality of operation boards, other than a last operation board, is connected, via a second inter-board path, to a next operation board of the plurality of operation boards, wherein an input object type of the first operation board comprises the first object type, wherein an output object type of each of the plurality of operation boards is an input object type of the next operation board,
wherein the plurality of operation boards corresponds to a plurality of operations, wherein the plurality of operations comprises a filter operation, a switch operation, and an enrich operation, wherein the plurality of operation boards comprises a filter operation board, an enrich operation board, and a switch operation board,
wherein the filter operation board comprises one or more filter elements connected, via one or more intra-filter operation board paths, by one or more logic operations, wherein the input type of the filter operation board and the output type of the filter operation board are identical,
wherein the switch operation board comprises (i) a first switch element representing the input object type of the switch operation board and (ii) a second switch element representing the output object type of the switch operation, wherein the first switch element and the second switch element are connected by a switch link element, via an intra-switch operation board path, representing a switch relationship between the input object type of the switch operation board and the output object type of the switch operation, and
wherein the enrich operation board comprises (i) a first enrich element representing the input object type of the enrich operation board, (ii) a second enrich element representing a second object type of the plurality of object types, or a combination thereof, and (iii) a third enrich element representing the output object type of the enrich operation board, the output object type of the enrich operation board comprising a virtual object type representing a combination of the input object type of the enrich operation board and the second object type, wherein the first enrich element and the second enrich element are connected, via a first intra-enrich operation board path, by an enriching link element representing an enrich relationship between the input object type of the enrich operation board and the output object type of the enrich operation board, and wherein the first enrich element is connected, via a second intra-enrich operation board path, to the third enrich element; and displaying the multi-level board user interface.

17. The method of claim 16, wherein:

the object board comprises an object board body; or each of the plurality of operation boards comprises an operation board header, an operation board body, and an operation board footer.

18. The method of claim 16, wherein the multi-level board user interface comprises the object board and operation boards of the plurality of operation boards that are arranged vertically.

19. The method of claim 16, further comprising:

generating an initial user interface comprising (i) the object board at the first display level connected to (ii) a plurality of selection elements at a second display level, wherein the plurality of selection elements corresponds to the plurality of operations; and providing the initial user interface for display to at least one device.

20. A non-transitory computer-readable storage medium including instructions that, when executed by at least one processor of a computing system, cause the computing system to perform a method comprising:

generating a multi-level board user interface comprising a plurality of boards at different display levels, the plurality of boards comprising (i) an object board at a first display level and (ii) a plurality of operation boards each at a different second display level, wherein the object board corresponds to a first object type of a plurality of object types comprising a patient object type, a treatment object type, and a diagnosis object type, wherein the object board is connected, via a first inter-board path, to a first operation board of the plurality of operation boards, wherein each of the plurality of operation boards, other than a last operation board, is connected, via a second inter-board path, to a next operation board of the plurality of operation boards, wherein an input object type of the first operation board comprises the first object type, wherein an output object type of each of the plurality of operation boards is an input object type of the next operation board, wherein the plurality of operation boards corresponds to a plurality of operations, wherein the plurality of operations comprises a filter operation, a switch operation, and an enrich operation, wherein the plurality of operation boards comprises a filter operation board, an enrich operation board, and a switch operation board, wherein the filter operation board comprises one or more filter elements connected, via one or more intra-filter operation board paths, by one or more logic operations, wherein the input type of the filter operation board and the output type of the filter operation board are identical, wherein the switch operation board comprises (i) a first switch element representing the input object type of the switch operation board and (ii) a second switch element representing the output object type of the switch operation, wherein the first switch element and the second switch element are connected by a switch link element, via an intra-switch operation board path, representing a switch relationship between the input object type of the switch operation board and the output object type of the switch operation, and wherein the enrich operation board comprises (i) a first enrich element representing the input object type of the enrich operation board, (ii) a second enrich element representing a second object type of the plurality of object types, or a combination thereof, and (iii) a third enrich element representing the output object type of the enrich operation board, the output object type of the enrich operation board comprising a virtual object type representing a combination of the input object type of the enrich operation board and the second object type, wherein the first enrich element and the second enrich element are connected, via a first intra-enrich operation board path, by an enriching link element representing an enrich relationship between the input object type of the enrich operation board and the output object type of the enrich operation board, and wherein the first enrich element is connected, via a second intra-enrich operation board path, to the third enrich element; and displaying the multi-level board user interface.

* * * * *